US008401871B2

(12) United States Patent
Fotsch et al.

(10) Patent No.: US 8,401,871 B2
(45) Date of Patent: Mar. 19, 2013

(54) HEALTHCARE NOTIFICATION METHOD AND SYSTEM INCLUDING A HEALTHCARE WEBSITE

(75) Inventors: Edward J Fotsch, Sausalito, CA (US); Debra Del Guidice, Sausalito, CA (US); Nick Krym, Castro Valley, CA (US); Leslie Yuan, San Francisco, CA (US)

(73) Assignee: PNC Bank, National Association, East Brunswick, NJ (US)

( * ) Notice: Subject to any disclaimer, the term of this patent is extended or adjusted under 35 U.S.C. 154(b) by 724 days.

(21) Appl. No.: 12/487,551

(22) Filed: Jun. 18, 2009

(65) Prior Publication Data

US 2009/0276243 A1 Nov. 5, 2009

Related U.S. Application Data

(63) Continuation-in-part of application No. 12/175,078, filed on Jul. 17, 2008, now abandoned, which is a continuation-in-part of application No. 11/086,118, filed on Mar. 21, 2005, now abandoned.

(51) Int. Cl.
*G06Q 10/00* (2012.01)
*G06Q 50/00* (2012.01)
*G06Q 40/00* (2012.01)

(52) U.S. Cl. ..................... 705/2; 705/3; 705/4
(58) Field of Classification Search .............. None
See application file for complete search history.

(56) References Cited

U.S. PATENT DOCUMENTS

| | | | |
|---|---|---|---|
| 4,319,336 A | 3/1982 | Anderson et al. |
| 5,478,211 A | 12/1995 | Dominiak et al. |
| 5,589,892 A | 12/1996 | Knee et al. |
| 5,597,072 A | 1/1997 | Lieberman et al. |
| 5,862,223 A | 1/1999 | Walker et al. |
| 5,899,998 A | 5/1999 | McGauley et al. |
| 5,930,759 A | 7/1999 | Moore et al. |

(Continued)

OTHER PUBLICATIONS

Irish Medicines Board, "The DATHS Communication System for Vigilance Issues" vol. 1 No. 7, Feb. 2004.*

(Continued)

*Primary Examiner* — Robert Morgan
*Assistant Examiner* — Eliza Lam
(74) *Attorney, Agent, or Firm* — Vierra Magen Marcus LLP

(57) ABSTRACT

Methods and apparatus enabling organizations with a need to communicate with healthcare providers regarding health-related issues affecting patient health to notify healthcare providers of a health-related issue affecting patient health are disclosed. An electronic notification of the health-related issue is transmitted by one of the organizations to a healthcare notification network, which may include a healthcare website, for transmission to a healthcare provider, where the electronic notification includes a mechanism for obtaining an acknowledgement indicating that the healthcare provider has received and opened the electronic notification. Healthcare related information, such as drug recalls and medication warnings to healthcare providers from content providers, along with other services, is provided at the healthcare website. Healthcare related information may also be provided through other websites, such as electronic prescription and electronic medical/health records websites. Other services include providing corresponding Continuing Medical Education ("CME") courses that may enable healthcare providers to earn CME credits toward a Maintenance of Certification (MOC) required by Medical Boards. MOCs for corresponding healthcare providers along with certificates to prescribe particular medications and/or use particular medical devices may be also stored at the healthcare website and verified by third parties, such as pharmacists and medical device manufacturers, before delivery.

30 Claims, 28 Drawing Sheets

U.S. PATENT DOCUMENTS

| | | | |
|---|---|---|---|
| 5,954,641 | A | 9/1999 | Kehr et al. |
| 5,974,389 | A | 10/1999 | Clark et al. |
| 6,039,688 | A | 3/2000 | Douglas et al. |
| 6,151,586 | A | 11/2000 | Brown |
| 6,171,112 | B1 | 1/2001 | Clark et al. |
| 6,208,973 | B1 | 3/2001 | Boyer et al. |
| 6,260,050 | B1 | 7/2001 | Yost et al. |
| 6,272,472 | B1 | 8/2001 | Danneel et al. |
| 6,381,029 | B1 | 4/2002 | Tipirneni |
| 6,516,315 | B1 | 2/2003 | Gupta |
| 6,654,724 | B1 | 11/2003 | Rubin et al. |
| 6,988,075 | B1 | 1/2006 | Hacker |
| 7,174,368 | B2 | 2/2007 | Ross, Jr. |
| 7,599,846 | B2 | 10/2009 | Fiedotin et al. |
| 7,659,826 | B2 * | 2/2010 | Humbard ............... 340/573.1 |
| 7,756,721 | B1 * | 7/2010 | Falchuk et al. ............... 705/2 |
| 2001/0056359 | A1 * | 12/2001 | Abreu ............... 705/3 |
| 2002/0072934 | A1 | 6/2002 | Ross et al. |
| 2002/0123909 | A1 | 9/2002 | Salisbury et al. |
| 2002/0128865 | A1 | 9/2002 | Alten |
| 2002/0128870 | A1 | 9/2002 | Whitson |
| 2002/0138306 | A1 | 9/2002 | Sabovich |
| 2002/0156650 | A1 | 10/2002 | Klein et al. |
| 2003/0018495 | A1 | 1/2003 | Sussman |
| 2003/0023269 | A1 | 1/2003 | den Boer |
| 2003/0023562 | A1 | 1/2003 | Bailey et al. |
| 2003/0028399 | A1 | 2/2003 | Davis et al. |
| 2003/0040940 | A1 | 2/2003 | Nehammer |
| 2003/0088440 | A1 | 5/2003 | Dunn |
| 2003/0088452 | A1 | 5/2003 | Kelly |
| 2003/0188200 | A1 | 10/2003 | Paquin et al. |
| 2003/0210147 | A1 | 11/2003 | Humbard |
| 2003/0214630 | A1 | 11/2003 | Winterbotham |
| 2003/0217109 | A1 | 11/2003 | Ordille et al. |
| 2004/0073453 | A1 | 4/2004 | Nenov et al. |
| 2004/0172307 | A1 | 9/2004 | Gruber |
| 2004/0186884 | A1 | 9/2004 | Dutordoir |
| 2004/0220829 | A1 | 11/2004 | Baharav et al. |

OTHER PUBLICATIONS

Non-Final Office Action dated Dec. 28, 2009, United States Patent & Trademark Office, U.S. Appl. No. 11/362,644, filed Feb. 27, 2006.
Non-Final Office Action dated Jan. 20, 2010, United States Patent & Trademark Office, U.S. Appl. No. 11/086,118, filed Mar. 21, 2005.
Rash, Wayne, "Interactive Voice Response Eases Drug Recall," www.eweek.com, Oct. 7, 2004, 2 pages.
Fiddleman, et al., "System Technology Can Improve Management of Product Alerts," ASHRM Journal 2004, vol. 24, No. 4, 4 pages.
"iMedica Gives Clinics Vital Edge During Vioxx Recall," PR Newswire, Oct. 4, 2004, 2 pages.
Final Office Action dated Jan. 29, 2010, United States Patent & Trademark Office, U.S. Appl. No. 11/208,144, filed Aug. 19, 2005.
Final Office Action dated May 25, 2010, United States Patent & Trademark Office, U.S. Appl. No. 11/085,984, filed Mar. 21, 2005.
Response to Office Action dated Jun. 28, 2010, U.S. Appl. No. 11/086,118, filed Mar. 21, 2005.
Fianl Office Action dated Aug. 20, 2009, United States Patent & Trademark Office, U.S. Appl. No. 11/086,118, filed Mar. 21, 2005.
Office Action dated Oct. 5, 2010, U.S. Appl. No. 11/086,118, filed Mar. 21, 2005.
Non-Final Office Action dated Nov. 27, 2009, United States Patent & Trademark Office, U.S. Appl. No. 11/085,984, filed Mar. 21, 2005.
Response to Non-Final Office Action dated Dec. 11, 2009, U.S. Appl. No. 11/086,118, filed Mar. 21, 2005.
International Search Report & The Written Opinion of the International Searching Authority dated Sep. 25, 2007, Patent Cooperation Treaty, Application No. PCT/US06/09968.
International Search Report & The Written Opinion of the International Searching Authority dated Sep. 24, 2007, Patent Cooperation Treaty, Application No. PCT/US06/31774.
Non-Final Office Action dated Jul. 26, 2007, United States Patent & Trademark Office, U.S. Appl. No. 10/641,982, filed Aug. 15, 2003.
Response to Non-Final Office Action dated Nov. 21, 2007, U.S. Appl. No. 10/641,982, filed Aug. 15, 2003.
Non-final Office Action dated Aug. 9, 2007, United States Patent & Trademark Office, U.S. Appl. No. 10/387,041, filed Mar. 10, 2003.
Response to Non-Final Office Action dated Dec. 10, 2007, U.S. Appl. No. 10/387,041, filed Mar. 10, 2003.
Final Office Action dated Mar. 5, 2008, United States Patent & Trademark Office, U.S. Appl. No. 10/387,041, filed Mar. 10, 2003.
Final Office Action dated Mar. 7, 2008, United States Patent & Trademark Office, U.S. Appl. No. 10/641,982, filed Aug. 15, 2003.
Acuff, Richard D., Fagan, M.D., Ph.D. Lawrence M., Rindfleisch, M.S., Thomas C. Levitt, Benajmin J., Ford, M.D., Paul M., "Lightweight, Mobile E-mail for Intra-Clinic Communication," Jun. 1997, Stanford University School of Medicine, Section on Medical Informatics, p. 4.
Schatz, Elizabeth, "Reaching a Doctor by E-Mail," Tuesday, Apr. 15, 2003, Wall Street Journal, p. 4.
Parker-Pope, Tara, "Virtual Second Opinions: When the Web Can Be Better Than Seeing a Local Doc," Health Journal, Aug. 2003.
Website, "The Healthy Email Project," [http://www.msu.edu/~healthy/page/project.html], Copyright 2001 Healthy Email Project, Michigan State University.
Website, "Powerful Technology Enabling Stronger Healthcare Partnerships," [https://www.mydoconline.com/Marketing/index.html], MyDocOnline (TM), tools for modern health care, Copyright 2003 MyDocOnline, Inc. All Rights Reserved.
Website, "Health Plan Benefits," Relay Health (SM) Secure Online Communication for Healthcare, [https://www.relayhealth.com/rh/specific/healthPlans/default.aspx], Copyright 1999-2003 Relay Health Corporation, All Rights Reserved.
Non-Final Office Action dated Feb. 18, 2009, United States Patent & Trademark Office, U.S. Appl. No. 11/068,118, filed Mar. 21, 2005.
US Food and Drug Admin., "Sign up for FDA's Free E-Mail Lists," navigated from www.recalls.gov obtained via http://web.archive.org for the date Mar. 19, 2004, http://web.archive.org/web/20040214031829/www.fda.gov/emaillist.html.
Vitros Immunodiagnostic Products, "Urgent Product Correction/Recall Notification," Oct. 25, 2004.
US Food and Drug Admin, "Patient and Physician Attitudes and Behaviors Associated With DTC Promotion of Prescription Drugs—Summary of FDA Survey Research Results," Nov. 19, 2004, Appendix B.3 2002 Physician Survey.
Response to Non-Final Office Action dated May 28, 2009, U.S. Appl. No. 11/086,118, filed Mar. 21, 2005.
Non-Final Office Action dated Jun. 23, 2009, United States Patent & Trademark Office, U.S. Appl. No. 11/208,144, filed Aug. 19, 2005.
U.S. Appl. No. 13/595,686, filed Aug. 27, 2012.
Nenadic et al., "Fair Certified E-mail Delivery" SAC '04, Mar. 14-17, 2004.
Office Action dated Aug. 3, 2010 in U.S. Appl. No. 12/175,078, filed Jul. 17, 2008.

* cited by examiner

Healthcare
Platform
Software
102a

| Healthcare Portal 200 | E-mail Alert And Notification 201 | Mobil Alert And Notification 202 | Content Management (CM) 203 |

| Rich Media 209 | Database 210 | Report and Business Intelligence (RBI) 204 |

| Support 208 | User Management 207 | Member Services 206 | Integration And Connectivity (IC) 205 |

| PHYSICIAN | SPECIALTY | PRESC. DRUGS/ EQUP.... | Com. Preference | CONTACT ADDRESS | DEFAULT/ PAPER ADDRESS |
|---|---|---|---|---|---|
| FOTSCH | EMERGENCY | LIDOCAINE... | E-MAIL | FTSCH@MEDEM.COM | 100 PINE, SF, CA 94111 |
| DEL GUIDICE | RADIOLOGY | ULTRASOUND... | FAX | 415.336.7878 | 54 MARKET, SF, CA 94111 |
| CHOY | INTERNAL | TACRINE... | SMS MESSAGE | 408.676.4960 | 2 MAIN, SJ, CA 95101 |

Database
210

Fig. 2B

Database 210

210a

| PHYSICIAN | SPECIALTY | PRESC. DRUGS/ EQUIP.... | Certifications Recieved | | | | Maintenance Of Certification (MOC) | MOC Information | Total Continuing Medical Education (CME) Credits Earned | Notifications Received | | | Associated Websites | |
|---|---|---|---|---|---|---|---|---|---|---|---|---|---|---|
| | | | 1 | 2 | 3 | 4 | | | | 1 | 2 | 3 | ERX | EHR |
| FOTSCH | EMERGENCY | LIDOCAINE... | Y | Y | N | Y | Current | ... | 100 | Y | Y | Y | Y | Y |
| DEL GUIDICE | RADIOLOGY | ULTRASOUND... | Y | N | Y | N | Current | ... | 138 | Y | N | N | Y | N |
| CHOY | INTERNAL | TACRINE... | N | Y | Y | N | Expired | ... | 87 | N | N | N | N | N |

210b

| Healthcare Notification | SPECIALTY | Continuing Medical Education (CME) Tests | Correct Answers | CME Credits Per Test |
|---|---|---|---|---|
| Notification 1 | EMERGENCY | Test 1 | Answers 1 | 10 |
| Notification 2 | RADIOLOGY | Test 2 | Answers 2 | 15 |
| Notification 3 | INTERNAL | Test 3 | Answers 3 | 10 |

210c

| MEDICATION/ MEDICAL DEVICE | Certification Tests | Correct Answers |
|---|---|---|
| LIDOCAINE | Test 1 | Answers 1 |
| PACEMAKER | Test 2 | Answers 2 |
| TACRINE | Test 3 | Answers 3 |

210d

| SPECIALTY | MOC Tests | Correct Answers |
|---|---|---|
| EMERGENCY | Test 1 | Answers 1 |
| RADIOLOGY | Test 2 | Answers 2 |
| INTERNAL | Test 3 | Answers 3 |

Fig. 2C

HTML Web page (Healthcare related notification) 500

ⓦHCNN
*Health Care Notification Network*

Current Alert | My Past Alerts | Health Alliance | My Privacy | My HCNN Account

Message Extras

More ZOVR Information

ZOVR Patient Information

Discuss ZOVR with colleagues

Report ZOVR Information

Pharmaceutical Company INC.
IMPORTANT DRUG INFORMATION

11/03/2007

Dear Healthcare Provider,

Pharmaceutical Company INC. would like to inform you of important changes regarding ZOVR(adfgres).The ZOVR prescribing information has been updated with the addition of the following information:

ADVERSE REACTIONS
Dermatologic
Allergic reactions such as urticaria have reported following initial or subsequent dosing when some patients are exposed to sunlight during the dosing period. Therefore patients should be informed and advised to avoid sun exposure during their treatment period.
This update is based on data reported in a recent large placebo controlled study (N=2000). Additional information on this and other clinical trials can be obtained by calling 1-800-xxx-yyyy.
We remind you that like other antibiotics in this class ZOVR is only indicated for serious soft tissue infections.
Pharmaceutical Company INC. remains committed to providing you with the most current product information available for the management of your patients. Please refer to the enclosed package insert for full prescribing information. As always, we request that serious adverse events be reported to Pharmaceutical Company INC. at 1-800-xxx-yyy or to the FDA MedWatch Program by Phone 1800-FDA1088, by FAX 1-800 FDA 0178 or by email www.fda.gov/medwatch.
For additional Medical information about ZOVR or any other Pharmaceutical Company INC. product, please call 1800-xxx-yyyy from 9am-5pm EST Monday through Friday.
Sincerely Dr xxxxxx.

Chief Medical Officer
Pharmaceutical Company INC.
Pharmaceutical company INC address

Services & Tools

Notifying Patients

Report Adverse Reaction and Observations

FDA Recalls / Safety Alerts

Order Medication Samples

Change Online Practice Profile

Save | File | Trash

Fig. 5A

Patient Healthcare related notification
501

HCNN Health Care Notification Network

Home | About Us | For Physicians | For Patients | Search | FAQs | Contact Us | Help

URGENT DRUG RECALL OR CORRECTION

Company ABC
101 Main Street
San Francisco, CA 94105                         Date: October 20, 2004

Dear Patient,

Company ABC Inc. would like to inform you of important changes regarding ZOVR (adfgres).

Allergic reactions such as urticaria (itching) have reported following initial or subsequent dosing when some patients are exposed to sunlight during the dose period. This is to inform you and you are advised to avoid sun exposure during the treatment period.

This information is based on data reported in a recent large study (N=2000) (NCT#XXXX, www.clinicaltrial.gov). Additional information on this and other clinical trials can be obtained by calling 1-800-xx-yyyy.

Company ABC Inc. remains committed to providing you with the most current product information available for the management of your condition. Please refer to the attached package insert for more information.

For additional medical information about ZOVR or any other Company ABC, Inc. product, please call 1-800-xxx-yyy from 9 am – 5 pm EST Monday through Friday.

Sincerely,

Dr. Xxxxx
Chief Medical Officer
Company ABC Inc.

Fig. 5B

HTML Web page
(Healthcare related notification with
Healthcare Provider Response Survey)
600

Fig. 6

Examples of HCNN NOTIFICATIONS
With FDA-Regulatory Compliance

HTML Email

Non-HTML Email with Link to HTML Web Page

HTML Web Page with NOTIFICATION

HTML NOTIFICATION with Physician Response Survey

Fig. 12

HEALTHCARE NOTIFICATION METHOD AND SYSTEM INCLUDING A HEALTHCARE WEBSITE

CROSS-REFERENCE TO RELATED APPLICATIONS

This application is a continuation-in-part of pending U.S. patent application Ser. No. 12/175,078, filed on Jul. 17, 2008 entitled, "HEALTHCARE NOTIFICATION METHOD AND SYSTEM INCLUDING A HEALTHCARE WEBSITE," which is a continuation-in-part of pending U.S. patent application Ser. No. 11/086,118, filed on Mar. 21, 2005 entitled, "HEALTHCARE NOTIFICATION SYSTEM."

This application is related to U.S. patent application Ser. No. 10/387,041, entitled "HEALTHCARE PROVIDER-PATIENT ONLINE CONSULTATION SYSTEM," filed on Mar. 10, 2003, naming Fotsch et al. as inventors, which is incorporated herein by reference for all purposes.

This application is also related to U.S. patent application Ser. No. 10/641,982, entitled "HEALTHCARE PROVIDER-PATIENT ONLINE CONSULTATION AND COMPLIANCE PROGRAM," listing Fotsch et al. as inventors, filed on Aug. 15, 2003, which is incorporated herein by reference for all purposes.

This application is also related to U.S. patent application Ser. No. 11/085,984, entitled "ELECTRONIC PERSONAL HEALTH RECORD SYSTEM," filed Mar. 21, 2005, naming Fotsch et al. as inventors, which is incorporated herein for all purposes.

This application is also related to U.S. patent application Ser. No. 11/208,144, entitled "ELECTRONIC PERSONAL HEALTH RECORD SYSTEM," filed on Aug. 19, 2005, naming Fotsch et al. as inventors, which is incorporated herein for all purposes.

This application is also related to U.S. patent application Ser. No. 11/362,644, entitled "METHOD, SYSTEM AND ARTICLE OF MANUFACTURE, SUCH AS A CARD, TO PROVIDE USER SELECTABLE MEDICAL INFORMATION AND INFORMATION TO OBTAIN ELIGIBILITY OF HEALTHCARE PAYMENTS," filed on Feb. 27, 2006, naming Fotsch et al. as inventors, which is incorporated herein for all purposes.

FIELD OF THE INVENTION

The present invention relates to online healthcare notification.

BACKGROUND

Timely, accurate, reliable and pervasive communication with physicians and patients is required for patient protection and safety, and for national defense against biological or communicable threats. But despite advancements in information and communication technology, most direct outreach to physicians and patients related to patient safety, product warnings or public health issues continue to rely on broadcast media and U.S. mail. Over 250 times each year, manufacturers, federal agencies and other third parties outreach directly to physicians, principally using the U.S. mail. Most of these messages relate not only to physicians themselves, but also directly to the patients in their care. These physicians, however, have no practical means by which to outreach to their patients and share the information, warnings, recalls or patient safety messages. In addition, mail-based physician outreach has inconsistent results and poor documentation.

Communicating efficiently and effectively with physicians and patients is critical to ensure patient and public safety. Manufacturers of healthcare products and services are at times required to contact physicians with information regarding their products and services. The information may be a product recall, warning, or other information of importance. In 2003 alone, there were a combined total of over 50 Class 1 FDA-mandated medication and device recalls, nearly all of which required direct notification of large numbers, typically hundreds of thousands, of physicians. In March 2004, over 100 medications had FDA-approved label changes, most related to new contraindications and warnings. Finally, it is estimated that over 25,000 safety reports on clinical trial investigational new drugs ("INDs") are sent annually. Currently, the principal method for communicating FDA-related product recalls or warnings directly to physicians is the U.S. mail. The current method for communicating FDA-related product recalls or warnings to patients/consumers is through press releases and media, and physician notification of their patients using telephone or U.S. mail.

In addition to FDA-related notifications, federal agencies and other public health advocates such as the Centers for Disease Control (the "CDC") also have a need to communicate rapidly with physicians in the event of a natural disaster, communicable outbreak, bioterrorism or other similar events. For the most part, current communication to physicians by government agencies related to emergent public safety is via media, fragmented outreach to local health systems, or the US Mail. Federally funded AHRQ studies from 2002 and 2004 demonstrated that while information technology held clear promise as a vehicle for physician communication in the event of emergent public health needs, the current notification systems are fragmented and under-funded, leaving the country and its citizens vulnerable.

As set forth above, there are many circumstances requiring that physicians or other individuals be contacted regarding situations affecting public health and safety. For instance, product recalls, warnings or label changes on medications may affect the health and safety of individuals taking these medications. Other possible scenarios affecting groups of individuals may include attempts at bio-terrorism or local epidemic outbreaks. In these circumstances, it is important to notify the affected individuals in a timely manner. The Federal Drug Administration (FDA) and the Centers for Disease Control (CDC) are among those charged with the responsibility of ensuring that members of the public are notified when these situations arise. Typically, organizations such as the FDA, the CDC, and pharmaceutical companies (among others) communicate with physician practices via U.S. mail. However, there is no way to ensure that the physicians have opened their mail. Moreover, there is generally a significant time delay between the time that mail is sent and the time that mail is received. In fact, after printing and handling, the U.S. mail typically takes several days to reach addressees. Moreover, U.S. mail that is not delivered appropriately often results in no, or delayed, notification to the sender. In some circumstances, Federal Express may be used in urgent situations. However, this option is costly and therefore only done in rare circumstances. Moreover, even with Federal Express, a day can be a significant amount of time when a person's health or safety is involved. In addition, physicians' addresses often change without timely notification. Even when the physician has received the mailed notification, there is no guarantee that the physician will open his or her mail, or that the appropriate patients will be notified by the physician. Unfortunately, there is currently no efficient mechanism in place to enable physicians to notify their patients, often resulting in further notifications to be sent via U.S. mail, if at all.

In conjunction with product recalls, warnings and other similar notifications, the FDA will often mandate that the responsible manufacturer conduct follow up studies to determine the efficacy of the mailing. These studies involve making contact with the physicians to ensure that the letter was received and read, and that the physician then notified his or her patients of the health-related issue addressed in the letter sent to the physician. While it is possible to confirm delivery of U.S. mail, this confirmation is limited to receipt of the mail piece only. Unfortunately, there is no efficient way for such a company to perform this research to ensure that the physician actually received and read the notification, and then took the appropriate measures to ensure that his or her patients were notified.

In addition, the physician may require more information than is typically contained in the notification, and because the notification is paper-based, several more steps are required for the physician to obtain access to this additional information.

It is also important to note that there is currently no mechanism in place for notifying the affected individuals, such as patients of physicians or those who care for them, of the types of developments set forth above, nor is there any way to effect broader outreach to all individuals in a particular area, for example, when a local or regional health crisis occurs. This is also true and becomes even more challenging on a nationwide scale, when notification might be required in the event of a bioterrorism event. For this reason and due to the time delays involved with mailing health-related notifications to physicians, the FDA and the CDC often turn to the media, such as television or radio, to notify the public of emergency or health-related situations. In this manner, the general public may be notified in a more efficient manner. Unfortunately, there is no guarantee that the notifications or warnings will reach the desired individuals. In view of the above, it would be beneficial if a more efficient mechanism for notifying physicians and patients of health-related matters could be implemented.

BRIEF DESCRIPTION OF THE DRAWINGS

FIGS. 2A-C illustrate a software architecture of healthcare platform software 102*a* illustrated in FIGS. 1A-B according to an embodiment.

FIG. 5A illustrates a healthcare related notification in the form of a HTML web page 500 provided at healthcare website 101 shown in FIGS. 1A-B according to an embodiment.

FIG. 5B illustrates a patient healthcare related notification 501 provided from a healthcare provider via healthcare website 101 shown in FIGS. 1A-B according to an embodiment.

FIG. 6 illustrates a healthcare related notification with a healthcare provider survey in the form of a HTML web page 600 provided at healthcare website 101 shown in FIGS. 1A-B according to an embodiment.

FIG. 12 illustrates an exemplary HTML web page 1200 that provides a CME test.

DETAILED DESCRIPTION

I. OVERVIEW

Figure 1A:
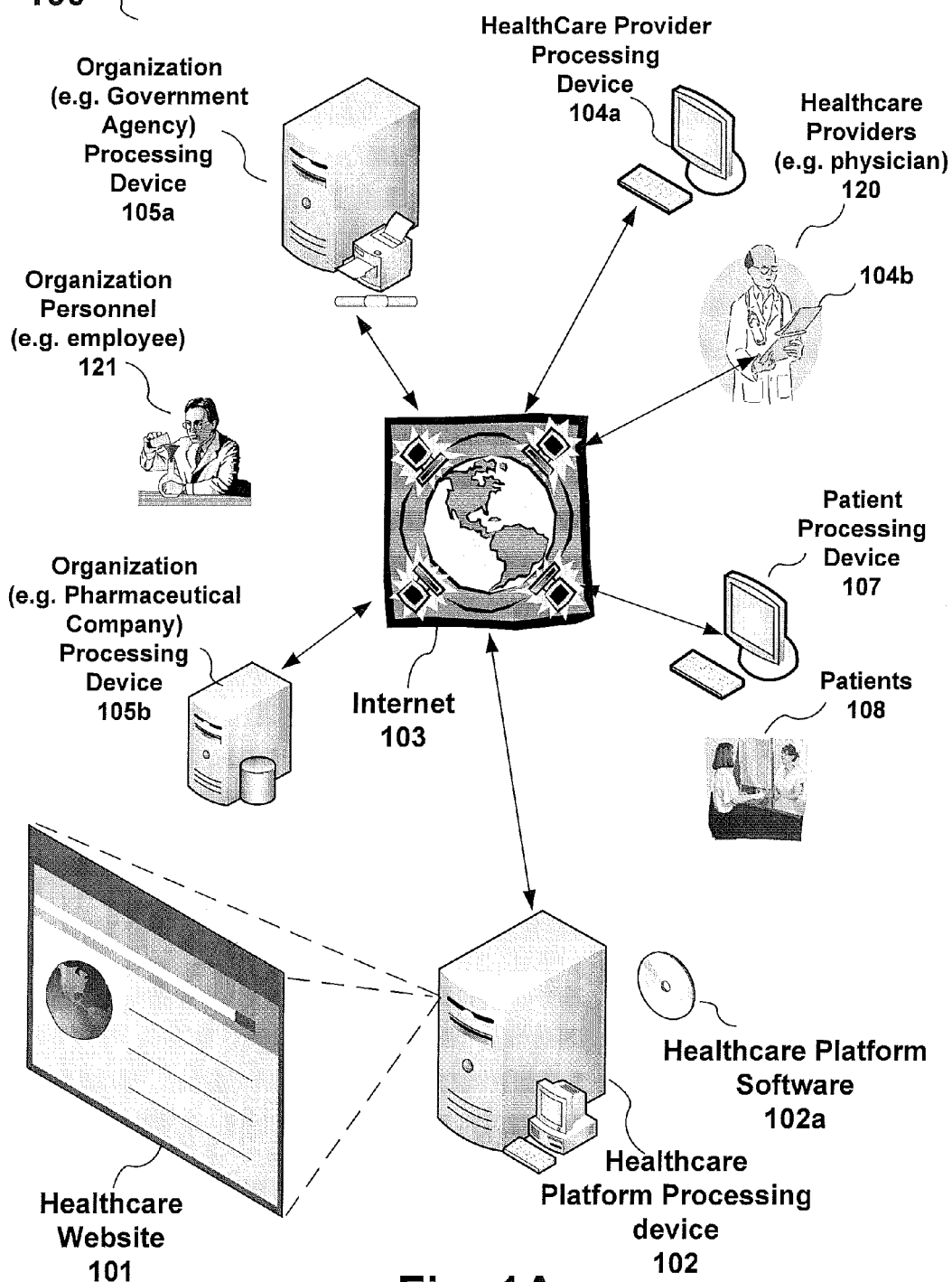
FIGS. 1A-C illustrate systems to distribute healthcare related information to healthcare providers and patients according to an embodiment.

A healthcare website (or portal) provides time-sensitive, safety healthcare related notifications from organizations, such as healthcare agencies, medical device manufacturers and pharmaceutical manufacturers, to healthcare providers, such as physicians. The healthcare related notifications (also referred to herein as notifications or healthcare notifications) may affect the patients of the healthcare provider or the general population. Acknowledgement of the notifications, along with a suite of services, is provided at the healthcare website for healthcare providers.

In an embodiment, the healthcare website is provided by a system including a healthcare platform processing device that is coupled to the Internet along with associated software that generates the notifications from organizations to healthcare providers along with the suite of services.

A medical event or issues affecting a patient or the general population health may arise under a variety of circumstances. For instance, it may be necessary to notify physicians of product recalls or label changes on medications, as well as provide education and certification requirements for certain existing/new medications (drugs) or medical devices. In particular, IND safety notices may be provided to physicians that result from a clinical trial of a drug and/or medical device. Other possible scenarios affecting the general population may include bio-terrorism outbreaks or local epidemics. The Federal Drug Administration ("FDA") and manufacturers are charged with the responsibility of notifying physicians and other healthcare providers and their patients in the event of a product recall, warning or label change, and the Centers for Disease Control ("CDC") and other government agencies bear the responsibility of notifying physicians and other healthcare providers and the public in the event of a local, regional or national public health threat. Thus, the organizations communicating with physicians via the healthcare website may include the FDA, CDC, and other federal agencies, as well as other companies or organizations, such as those that are governed by the FDA. The terms healthcare provider and physician will be used interchangeably herein. However, it is important to note that the healthcare provider need not be a physician.

In accordance with an embodiment, FDA regulatory requirements are fulfilled and include notifying physicians of health-related issues with and/or changes to the use of products that could impact patient safety. The FDA regulatory requirements also include a follow-up aspect ensuring that the physicians received the notification transmitted to them and that their patients were notified. In order to satisfy these regulatory requirements, a notification and acknowledgement system is provided as described in further detail below.

In accordance with another embodiment, a notification system and method is provided that enables organizations such as the CDC or FDA (or companies governed by the FDA) to make contact with physicians regarding issues affecting patient health. In an embodiment, the notification system and method enables a notification to be generated and transmitted via electronic mail on behalf of an organization to physicians. The electronic mail will include a link to the healthcare website that includes the notification, as well as a suite of other services. In an embodiment, the electronic mail (or other type of electronic message such as text message) may include a link directly to the healthcare notification.

In an embodiment, an acknowledgement is provided that enables an acknowledgement message to be transmitted back to the healthcare website (or in particular the healthcare platform processing device) and then reported to the corresponding organization. The acknowledgement message may be transmitted automatically or in response to input by the healthcare provider. In an embodiment, the acknowledgement message will indicate that the healthcare provider has received and opened the notification message. In another embodiment, the acknowledgement message may indicate that the healthcare provider has read and understands the notification. In yet another embodiment, the acknowledgement message may indicate that the healthcare provider will follow or has followed the instructions provided in the notification message or, alternatively, that the healthcare provider will notify or has notified patients of the issue affecting patient health that has been identified in the notification message.

In an embodiment, the healthcare website provides certifications to healthcare providers. In an embodiment, only healthcare providers that have been certified (or have a certification) for a particular medication and/or medical device are allowed to prescribe the particular medication and/or use the particular medical device on a patient. In an embodiment, a delivery agent, such as a pharmacist and/or medical device manufacturer, would not fill a prescription for a particular medication or provide the medical device unless the certification of the healthcare provider is verified by way of an electronic database. For example, a healthcare provider may be certified after one or more of the following occurs: 1) the healthcare provider reviews education material regarding the medication and/or medical device (that may be provided with healthcare notifications in an embodiment); 2) the healthcare provider passes a test covering the education material; 3) the healthcare provider ensures that the patient is educated regarding the medication and/or medical device; and 4) a document describing the medication and/or medical device including its risks and side effects has been read, understood, accepted, signed and stored in a patient's medical record, such as an electronic medical record. In an embodiment, a delivery agent would not fill the prescription for the medication and/or provide the medical device without verifying that not only the healthcare provider is certified, but that the patient has been certified as well. In an embodiment, a patient may be considered certified by having a signed document as described above stored in the patient's medical records that may be verified by the delivery agent.

In an embodiment, certification of a healthcare provider for a particular medication and/or medical device is provided at least partly by the healthcare website. Certifications for both healthcare providers and patients may be stored in an electronic database. The certifications may then be accessed and verified by delivery agents, such as pharmacists and medical device manufacturers.

In an embodiment, the healthcare website provides Continuing Medical Education ("CME") information and/or tests including questions associated with the healthcare notifications. A healthcare provider may take the tests after reviewing the healthcare notifications in order to satisfy requirements for license renewal or specialty certification (i.e. general CME as well as CME required for Maintenance of Certification ("MOC") by medical boards). The healthcare website may compare healthcare provider's answers with correct answers in order to award credits. Upon successful completion of CME tests, earned credits by the participating healthcare providers may be stored in and accessed from the healthcare website. In yet another embodiment, the status of other MOC requirements may be stored and accessed from the healthcare website. Different requirements may be required by different medical boards. For example, the American Board of Surgery may have different MOC requirements and different MOC tests than the American Board of Internal Medicine. Other MOC requirements may include verification of the healthcare provider's 1) good medical standing, such as an unrestricted license, hospital privileges and satisfactory references; and 2) practical performance evaluations that may include evaluations of professionalism and communication.

In an embodiment, the healthcare website may provide healthcare notifications by way of other associated healthcare websites, such as electronic prescription ("ERX") and health/medical records ("EHR') websites. An indication that a healthcare notification is available may be provided to healthcare providers at these associated healthcare websites depending upon whether the healthcare provider has already viewed the healthcare notification. For example, a healthcare provider would not receive an indication of the healthcare notification when the healthcare provider has already reviewed the healthcare notification by way of an acknowledged email. Healthcare providers may access the healthcare notifications from the associated healthcare websites by either registering or logging into the healthcare website from the associated healthcare website. In an alternate embodiment, a hyperlink to the healthcare notification may be provided to selected healthcare providers at the associated healthcare websites.

Other services provided at the healthcare website may include accesses to related literature or a dialogue with peers or other healthcare providers regarding the notification or topics of a general nature. Access to other important information may influence the healthcare provider's action with regard to the received notification information.

In accordance with an embodiment, healthcare providers have access to a patient version of the notification and the ability to send the patient version to predetermined patients. This may be accomplished via a network in which the healthcare provider and the patients are members. (This network may be included in the system having the healthcare platform processing device, or a different network, from the system used by organizations to reach healthcare providers with the notification messages.) A healthcare provider may choose to send a notification message to all of their patients. Alternatively, a healthcare provider may select to identify the patients, to which the health-related issue pertains, thereby enabling the healthcare provider to send a notification message to a predetermined subset of patients.

In accordance with an embodiment, a healthcare provider may identify a subset of patients via an electronic health record system (or electronic database) that stores a plurality of patient records. By searching the online health record system, a healthcare provider may identify the subset of patients to which the health-related issue pertains.

Healthcare providers may have important information to share with the notifying organizations, regarding such things as adverse events or reactions, community observations, and other information that is crucial and time-sensitive. An additional service is provided to healthcare providers to share this important and time-sensitive information with the appropriate third parties. In accordance with yet another aspect of the invention, the healthcare website will provide physician-organization communications to report adverse reactions to medications and devices; healthcare findings resulting from a local or regional biological/communicable threats, outbreaks or other crisis. This reporting may be related to a current or prior notification or may be unrelated to the notification. This reporting may be to the appropriate pharmaceutical company or medical device manufacturer, federal agency including but not limited to the FDA, CDC, and other organizations that the physician desires to notify.

Still another service includes allowing healthcare providers access to pharmaceutical samples, when one being prescribed is recalled, has a black-box warning or label change that requires the physician to turn to another drug for his/her patients or when a physician needs medication available to treat local or regional disease outbreaks, bio-terrorism or other threats to patient safety. Facilitating access to sample ordering will allow healthcare providers to effectively and efficiently get to know new medications and facilitate patient access to medications immediately upon diagnoses.

In an embodiment, the healthcare website enables peer review of communications between organizations and healthcare providers. In particular, although healthcare providers may have direct access to the healthcare website to transmit messages, organizations may submit communications from healthcare providers for review by others before they can be transmitted to other healthcare providers. Others, or a governing body, then review the communications to ensure that it meets criteria for delivery to healthcare providers. When the communications meet the criteria, the communications or a portion thereof is transmitted to healthcare providers. Similarly, when responses or acknowledgments are received from healthcare providers, these responses may be compiled by the individuals associated with the organizations with regard to "fulfillment" of the action required of the communication.

Another service at the healthcare website allows healthcare providers the ability to refer back to notifications that have been sent. The ability to create a healthcare provider-specific repository of prior notifications for their reference purposes is important to the continued safe prescribing and monitoring of prescription drugs and medical devices, and to the continued safe practice of medicine for a physician, while treating a patient where a notification contains information that may validate an observation of a patient or population. Still yet another service, allows healthcare providers to save, file, or delete notifications, and retrieve notifications from their files for reference at a later date.

Another service at the healthcare website allows healthcare providers the ability to update their notification profile, to ensure its currency. Accordingly, time critical notifications will be provided in a manner that is most efficient for that particular healthcare provider. For example, one physician may prefer the notification sent directly to a wireless handheld device; while another physician would prefer the notification be provided to his office computer. In each case, the physician will receive the notifications in the most efficient manner based on the physician's practice.

Another service at the healthcare website allows healthcare providers the ability to update their practice profile to ensure its currency. This practice profile may be included in healthcare platform software 102a or may be a profile used to provide practice information to patients and other healthcare providers from another source.

In an embodiment, the functionality of the healthcare website may be integrated into a portlet or applet within third party systems or applications, including but not limited to physician practice electronic medical/health record systems, practice management systems, and other third party systems. For example, an applet is embedded into an application to facilitate access to notifications. Notifications may be integrated into the workflow of an application so that the notifications are provided by way of a message inbox or task bar.

In the following description, numerous specific details are set forth in order to provide a thorough understanding of embodiments. It will be obvious, however, to one skilled in the art, that embodiments may be practiced without some or all of these specific details. In other instances, well known process steps have not been described in detail in order not to unnecessarily obscure a particular embodiment.

The present embodiments, among other embodiments, describe online healthcare provider-organization notifications and acknowledgements via the Internet. In an example, the healthcare provider is a physician. Thus, the following example will refer to physician-organization communications. The terms healthcare provider and physician will be used interchangeably herein. However, it is important to note that the healthcare provider need not be a physician.

II. SYSTEM

FIG. 1A illustrates a system 100 that provides time critical healthcare related information, along with other healthcare related services, in an efficient and timely manner to one or more selected healthcare providers 120. System 100 provides healthcare related electronic notifications from organizations or organization personnel 121 (via at least one organization processing device 105a/105b)) to selected healthcare providers 120 (via at least one healthcare processing device 104a-104b) based on the subject matter of the notice. In an embodiment, system 100 provides acknowledgement messages from a healthcare provider processing device that may include healthcare provider survey answers in response to receiving the healthcare related notification. Healthcare providers 120 may also generate healthcare related notifications to selected patients 108 (via at least patient processing device 107) based on the subject matter of the notification. System 100 includes a healthcare website 101 to provide healthcare related notifications including other healthcare related services to healthcare providers 120 and organization personnel 121.

Healthcare website 101 including healthcare related services are provided by healthcare platform processing device 102 and associated healthcare platform software 102*a*. For convenience, information is described herein as being transferred to and from healthcare website 101; however, one of ordinary skill in the art understands that information is actually transferred to and from healthcare platform processing device 102. Similarly for convenience, healthcare website 101 is described herein as processing information when in actuality processing device 102 and associate healthcare platform software 102*a* is actually performing the processing.

Figure 9:
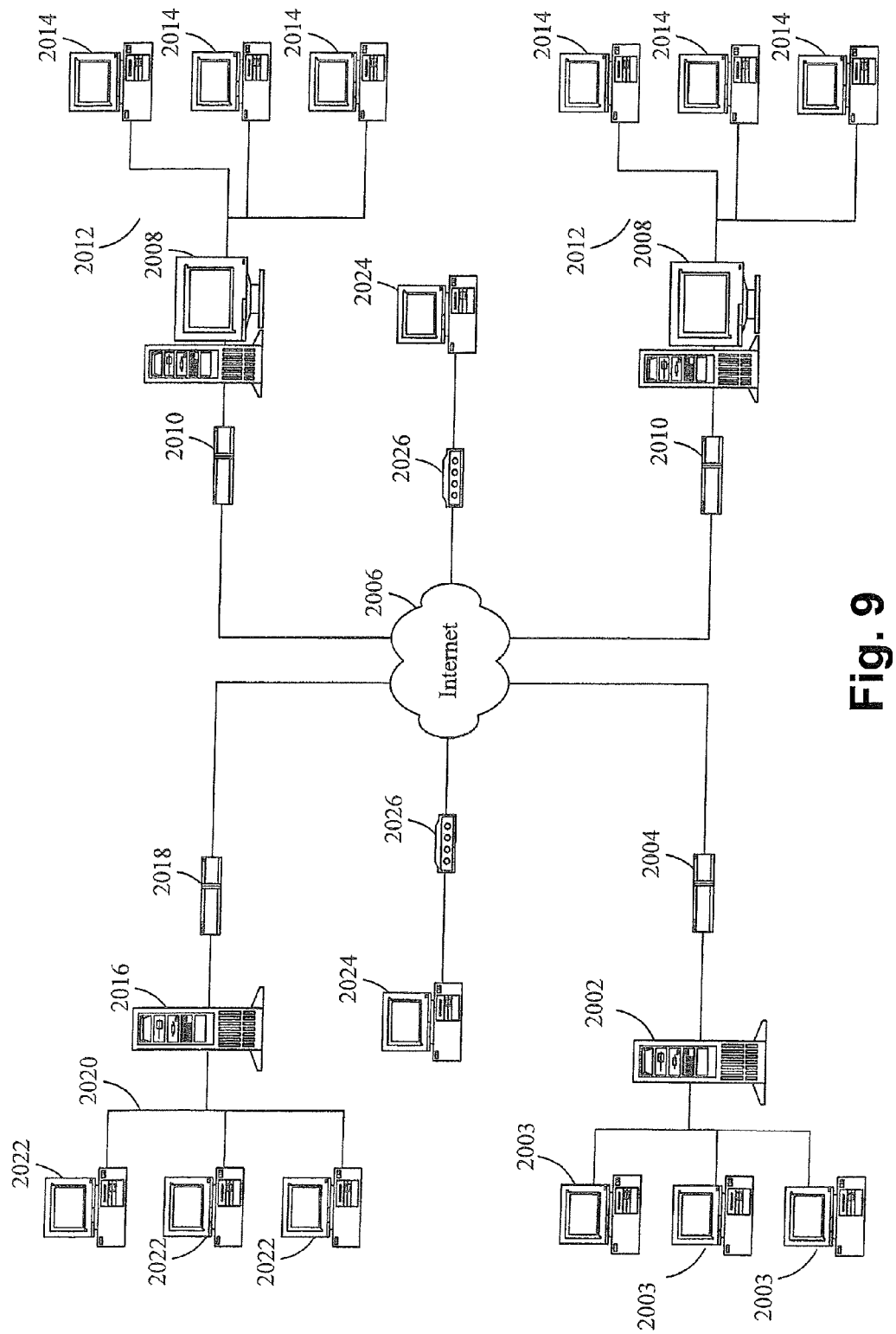
FIG. 9 is a diagram illustrating an exemplary system according to an embodiment.
Figure 10:
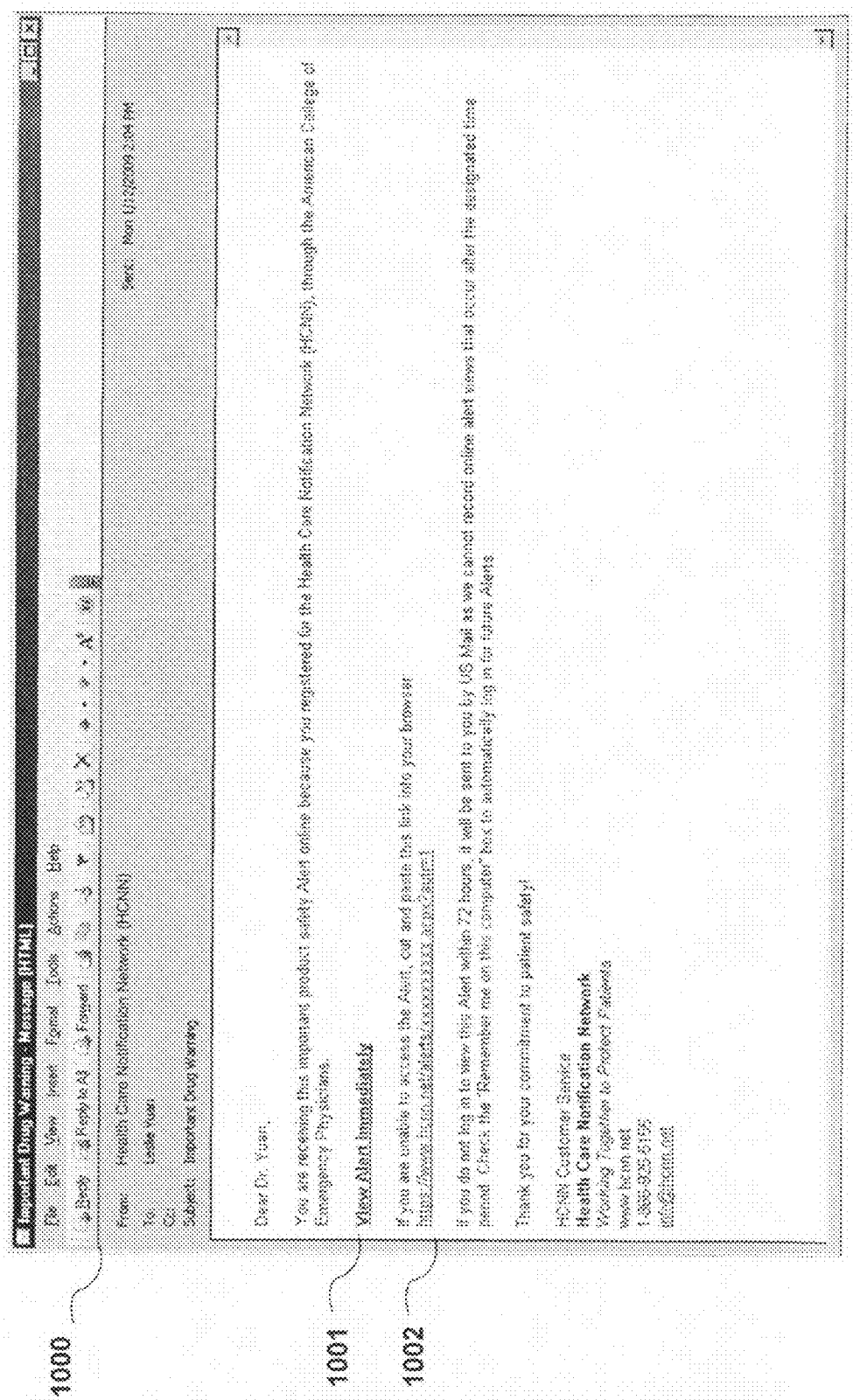
FIG. 10 illustrates an exemplary email 1000 alert to an emergency physician that includes a link 1001 to a HTML web page having a healthcare related notification.

In an embodiment, processing devices 105*a/b*, 104*a/b*, 107 and 102 are coupled and communicated by way of Internet 103. In alternate embodiments, healthcare platform processing device 102 and associated healthcare platform software 102*a* are included in a healthcare notification network as illustrated in FIG. 9 and described below in detail. In embodiments, system 100 may have far greater or fewer processing devices. In embodiments, a processing device may represent multiple hardware components or a network of distributed processing devices or hardware components. Processing devices may be coupled to Internet 103 by way of a wired or wireless connection, singly or in combination.

Healthcare website 101, in an embodiment, is a collection of healthcare related web pages, images, videos or other digital healthcare related services that is hosted on one or more processing devices and is accessible via the Internet 103 by client processing devices. In an embodiment, a web page is a digital document that may be written in HTML (Hypertext Markup Language) or an equivalent. The HTML document may be accessible via HTTP (Hypertext Transfer Protocol), a protocol that transfers information from a processing device to another processing device in response to a request. In an embodiment, one or more processing devices in system 100 include a HTML-compatible browser to view HTML web pages. In an embodiment, HTML documents are provided from at least processing device 102 to processing devices 105*a-b*, 104*a-b* and 107 in response to a request. HTML provides basic document formatting and allows "links" or "hyperlinks" to other processing devices (or servers) and files. A link such as a Uniform Resource Locator ("URL") has a specific syntax that identifies a network path to a server for defining a network connection. Embedded hyperlinks on a given web page can be used to find information related to the given web page. By clicking on a hyperlink in one web page, the user can display another related web page or even invoke a related software program.

In embodiments, a processing device may include a mainframe computer, server, laptop computer, hand-held computer, personal digital assistant, a facsimile machine, a telephone, a cellular telephone, a pager, short message service (SMS) messaging device, email device, an information appliance, or an equivalent. In an embodiment, a processing device includes at least one integrated circuit processor that executes machine readable instructions or software stored on a storage device.

In an embodiment, an organization may include a pharmaceutical company, medical device manufacturer, medical equipment manufacturer, government organization, or medical society; while healthcare providers may include physicians, physician assistants, non-prescribing individuals associated with clinical trials, etc.

Healthcare website 101 (via healthcare platform processing device 102 and software 102*a*) provides a number of functions/services to content consumers, such as organizations, delivery agents and healthcare providers. In embodiments, healthcare website 101 provides the following services to content consumers:

1) Register, create and maintain a content consumer account with pertinent and up-to-date contact/profile information;

2) Real-time electronic notifications to selected healthcare providers regarding healthcare issues with a backup paper based system;

3) Self-managed repository of notifications for future reference;

4) Reference website for access to healthcare information such as information related to product recalls and/or alerts, with robust search functionality;

5) Online provider of resources to obtain additional information on any product, ranging from informational brochures, videos, product samples;

6) Portal which allows access for healthcare providers to connect to other healthcare providers in order to report adverse events, communicate warnings securely to patients and join or initiate discussions with other healthcare providers;

7) Provide CME information including tests associated with healthcare notifications as well as award and store CME credits in response to healthcare providers completing the tests;

8) Provide healthcare notifications to related healthcare websites, such as ERX and EHR websites, based on whether the selected healthcare provider had received the healthcare notification;

9) Provide certifications for healthcare providers and/or patients as well as store such information for access by delivery agents, such as pharmacists and medical device manufacturers; and 10) Provide information to obtain a healthcare provider's MOC and store the status of requirements to obtain the healthcare provider's MOC, such as at least whether the required test to obtain a MOC has been passed by the healthcare provider.

In embodiments, healthcare website 101 provides the following services to content providers, such as organizations:

1) Access to healthcare providers to disseminate critical healthcare notifications such as drug recalls or bioterrorism;

2) Tools to provide content, such as healthcare notifications, to selected healthcare providers; and 3) Access to reporting tools to monitor receipt of the healthcare notifications.

In an embodiment, healthcare platform processing device 102 has associated individuals or an organization that is charged with governing, enabling, supporting and providing other operational activities to the healthcare website 101.

Figure 1B:
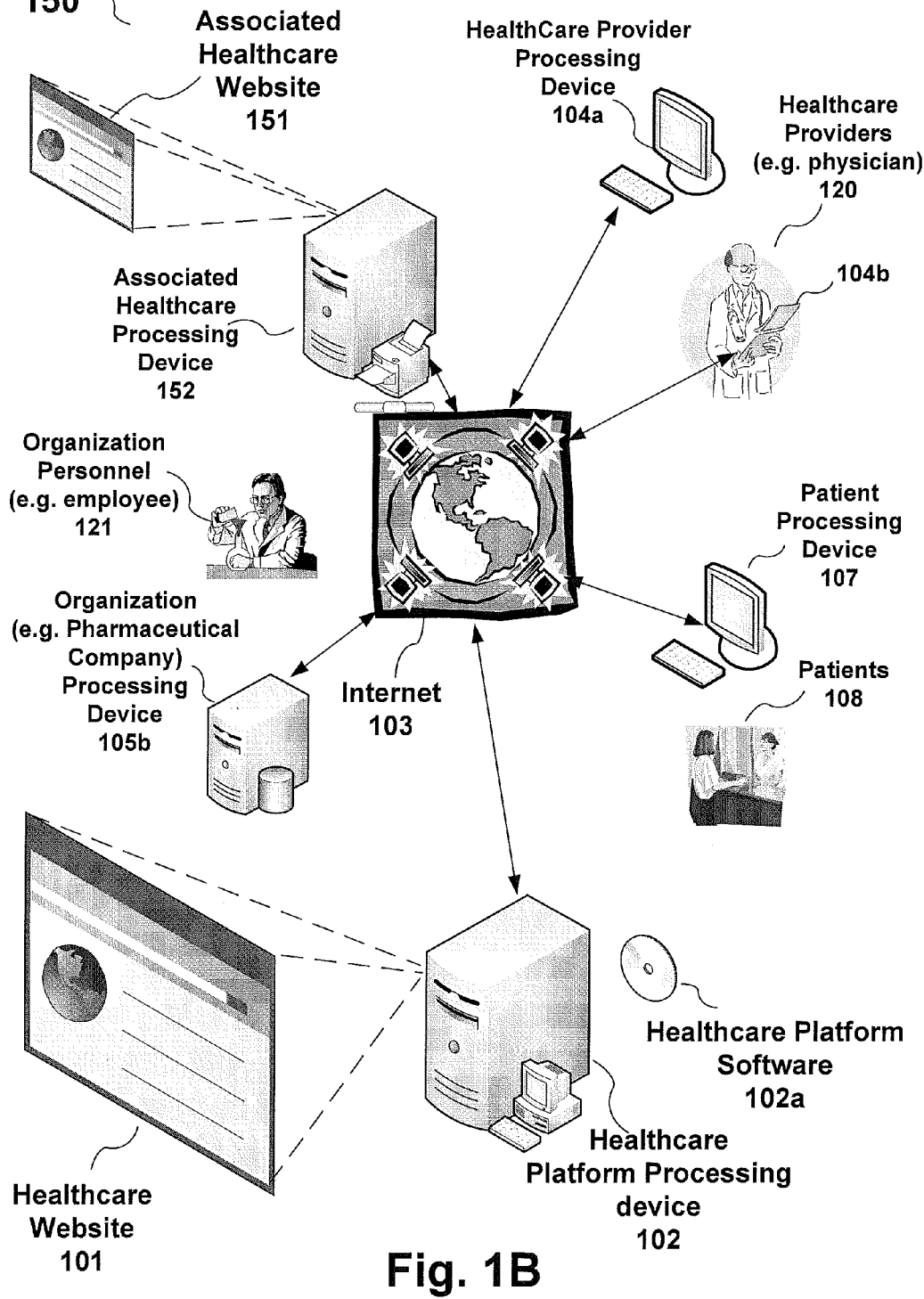

FIG. 1B illustrates a system 150 similar to system 100 shown in FIG. 1A except that an associated processing device 152 provides an associated healthcare website 151. In an embodiment, associated healthcare website 151 is an ERX and/or EHR website. Processing device 152 executes machine readable instructions or software stored on a storage device to communicate with healthcare website 101 as well as other processing device shown in FIG. 1B by way of Internet 103 as described herein. In an embodiment, an ERX service or website provides healthcare providers 120 with the function of providing prescriptions electronically. In an embodiment, an EHR service or website stores and provides electronic health or medical records of patients 108 that may be accessed by healthcare providers 120.

Figure 1C:
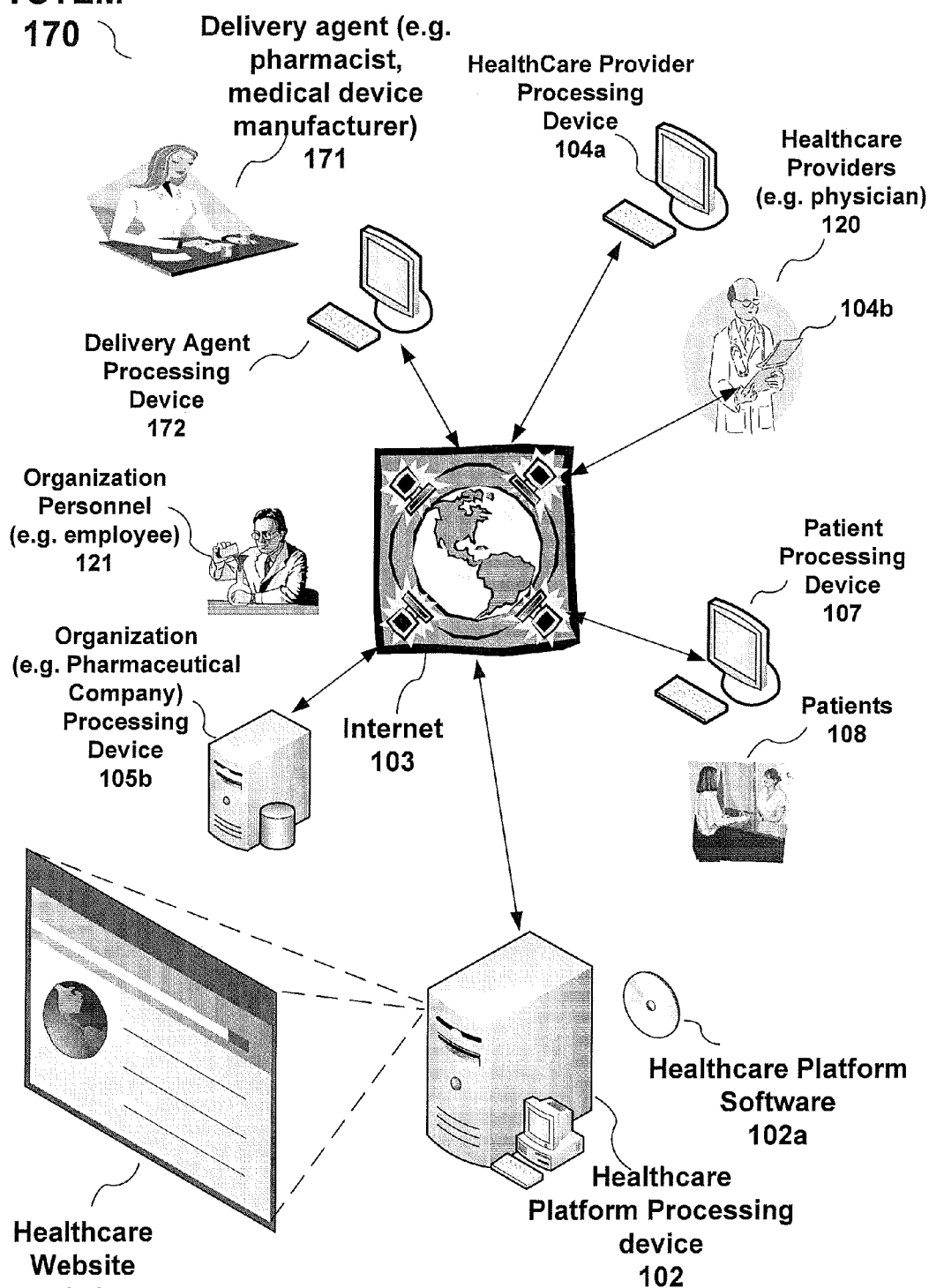

FIG. 1C illustrates a system 170 similar to system 150 shown in FIG. 1B except that a delivery agent processing device 172 and delivery agent 171, such as a pharmacist and/or medical device manufacturer replaces associated processing device 152 and associate healthcare website 151. In an embodiment, system 150 and 170, as well as other systems described herein may be combined singly or in combination in various embodiments. In an embodiment, healthcare provider(s) 120 by way of healthcare provider processing device 104a and Internet 103 access healthcare website 101 in order to obtain a certificate to prescribe a particular medication to a patient and/or use a particular medical device on a patient. As described in detail below, healthcare provider(s) 120 obtains a certificate for a particular medication and/or medical device by passing a test provided by healthcare website 101. The certificate is then stored in an electronic database of healthcare platform processing device 102. Delivery agent 171 may access the electronic database by way of delivery agent processing device 172 and healthcare website 101 in order to verify healthcare provider(s) 120 is certified for a particular medication before filling a prescription for a patient(s) 108 of healthcare provider(s) 120 or shipping a medical device to be implanted or provided to patient(s) 108 by healthcare provider 120. In embodiments, a medical device may be any object used for medical purposes on a patient. A medical device may be implanted during surgery or used for diagnosis or therapy. For example, a medical device may be, but not limited to, a pacemaker, stent, catheter or ultrasound machine.

FIGS. 3A-G illustrate methods 300, 320, 350, 370, 380 and 390 according to embodiments. In an embodiment, FIGS. 3A-G illustrate the operation of systems 100, 150 and 170 shown in FIGS. 1A-C. As one of ordinary skill in the art would appreciate, FIGS. 3A-G illustrate logic boxes or steps for performing specific functions. In alternate embodiments, more or fewer logic blocks or steps are used. In an embodiment, a logic block or step may represent at least partial execution of a software component as well as execution of a hardware operation or user operation, singly or in combination. For example, many logic blocks in FIGS. 3A-G represent the execution of software components illustrated in FIG. 2A on processing device 102 shown in FIG. 1A. In regard to FIG. 3A, logic block 306 illustrates a creation of a healthcare account at website 101. In an embodiment, individual healthcare providers create an account at website 101. In an embodiment, a healthcare organization, such as a medical society, health system, physicians group and/or an equivalent, pre-register their members as illustrated by logic block 306. The healthcare organization provides a data file to website 101 to create respective healthcare accounts. Website 101 then may generate respective emails to the members of the healthcare organization so that the members may complete the registration or healthcare account creation process.

Logic block 301 illustrates an organization, such as a pharmaceutical company, using system 100 to issue a healthcare related notification to healthcare providers having accounts, such as a recall of a drug used by anesthesiologists. A representative of the pharmaceutical company uses system 100 to submit a recall or health notification as illustrated by logic block 302. The representative specifies important parameters of the recall, data and other content associated with the recall, as well as criteria for recipients. The parameters associated with the recall also include the date/time of activation. The proposed notification is reviewed as illustrated by logic block 303. In an embodiment, a government agency or peer review board reviews the notification. If the notification is rejected, the notification is not sent as illustrated by logic block 304. In an embodiment, the rejected notification is sent back to the organization with an explanation of the rejection so that the third party may revise and resubmit another healthcare notification and logic blocks 301-303 may be repeated.

At the time of activation, as illustrated by logic block 309, healthcare system 100 makes recall data available to the selected group of content consumers which in this case includes anesthesiologists and possibly other specialists at healthcare website 101 for viewing.

At the same time, system 100 sends email to individuals within the group for whom it has email addresses as illustrated by logic block 305. Healthcare website 101 may also send FAXs to some of the healthcare providers, or messages to their mobile devices based on the communication preference of the respective healthcare providers. In other embodiments, a pager or other electronic means may be used. Healthcare website 101 resends notifications in the event of a delivery failure. Upon several successive failures, the website 101 would notify a content consumer via standard mail. Some content consumers will have no means of electronic communication. In that case, a process of sending standard mail communication performed by a personnel supporting healthcare website 101 is triggered.

Logic block 307 illustrates a healthcare provider receiving an electronic message, such as an email, regarding a healthcare notification. Upon receipt of the electronic message, the healthcare provider may read detailed information or may log into the healthcare website 101 to view the full notification as illustrated in logic blocks 308 and 309.

Healthcare providers that did not receive an electronic message regarding a healthcare notification may also view the notification as illustrated by logic blocks 310 and 309.

Also, organizations may log into healthcare website 101 to view statistics, such as the number of healthcare providers that have received a particular healthcare notification as illustrated by logic blocks 311 and 312.

Logic block 315 illustrates that healthcare website 101 receives an acknowledgment that the selected healthcare provider has read the healthcare notification. The selected healthcare provider then may access other functions/services 130 at healthcare website 101 that may be related to the healthcare related notification. A healthcare provider may access services 130 that are not related to the healthcare notification as illustrated by separate logic block 316.

Figure 3A:
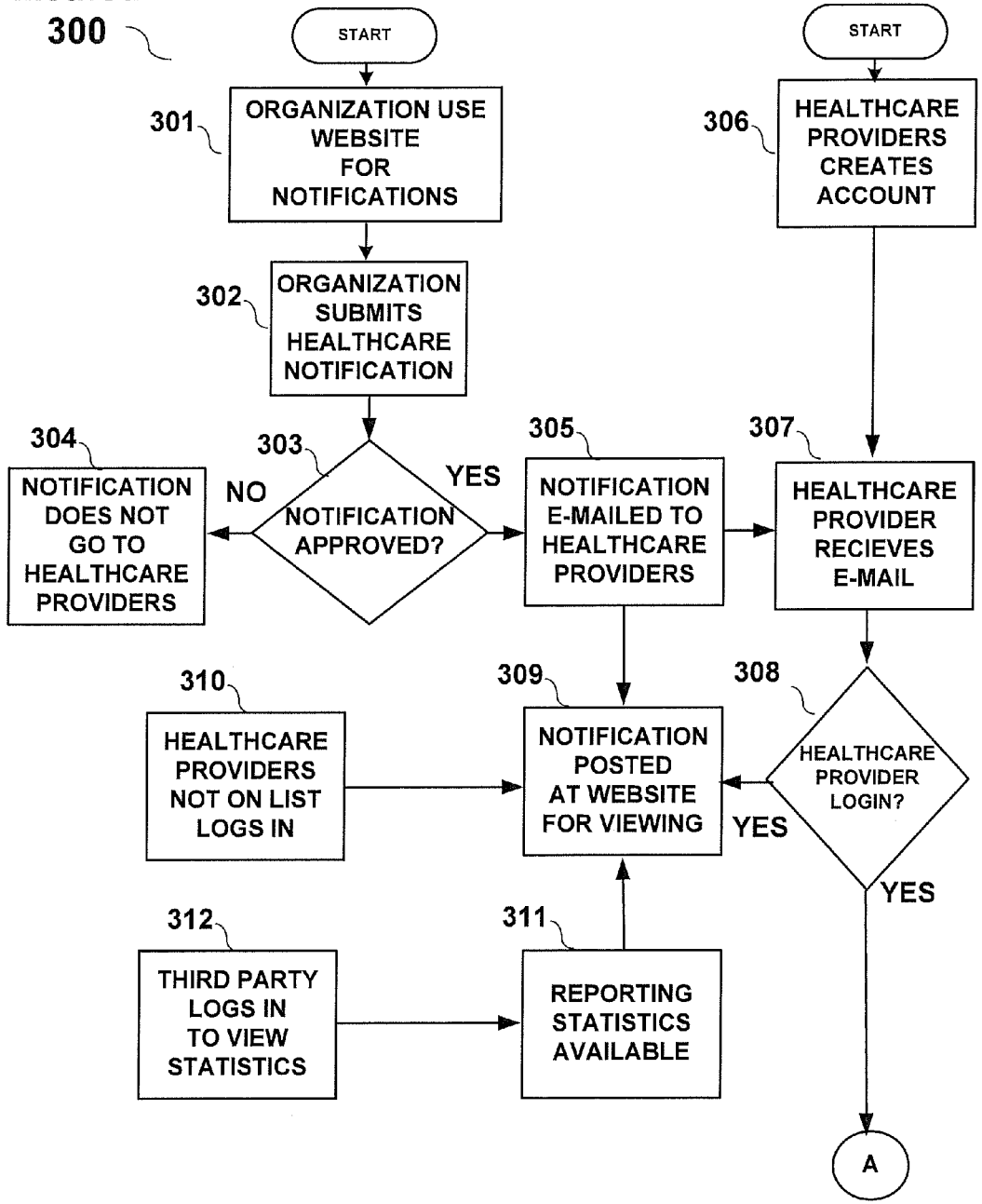
FIGS. 3A-G are flow charts to illustrate distributing healthcare related information to healthcare providers and patients according to an embodiment.
Figure 3B:
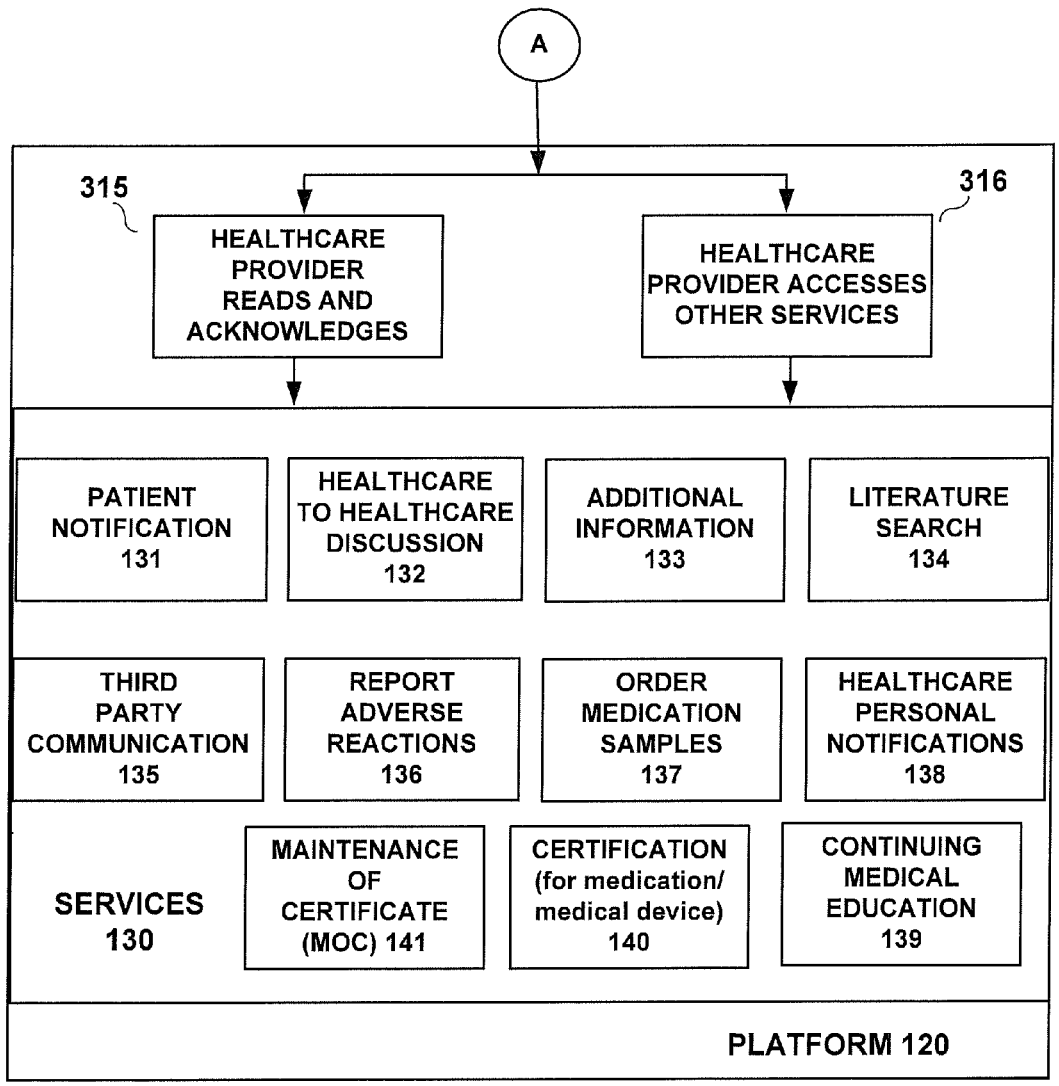

Logic blocks 131-139 shown in FIG. 3B represent a suite of services or functions provided at healthcare website 101. One of ordinary skill in the art understands that more or less services may be provided in embodiments.

Logic block 131 illustrates a service for a healthcare provider to transform the received healthcare notification to a notification for a patient or a selected subset of patients interested in the healthcare notification.

Logic block 132 illustrates a service for a healthcare provider to initiate or join a discussion with other healthcare providers regarding the healthcare notification or on another topic.

Logic block 133 illustrates a service for a healthcare provider to access additional information related or not related to the healthcare notification.

Logic block 134 illustrates a service for a healthcare provider to access a search program to obtain related literature or not related to the healthcare notification.

Logic block 135 illustrates a service for a healthcare provider to communicate with third parties, such as organization, regarding or not regarding the healthcare notification.

Logic block 136 illustrates a service for a healthcare provider to report adverse reactions to third parties.

Logic block 137 illustrates a service for a healthcare provider to order medication samples.

Logic block 138 illustrates a service for a healthcare provider to access previously received healthcare notification.

Logic block 139 illustrates a service for a healthcare provider to earn and view CME credits.

Logic block 140 illustrates a service for providing a healthcare provider with a certification to prescribe a particular medication and/or use a particular medical device as well as allow verification by delivery agents.

Logic block 141 illustrates a service for providing a healthcare provider (as well as third parties) with information (including a test to pass) regarding the status of the healthcare provider's MOC.

Figure 3C:
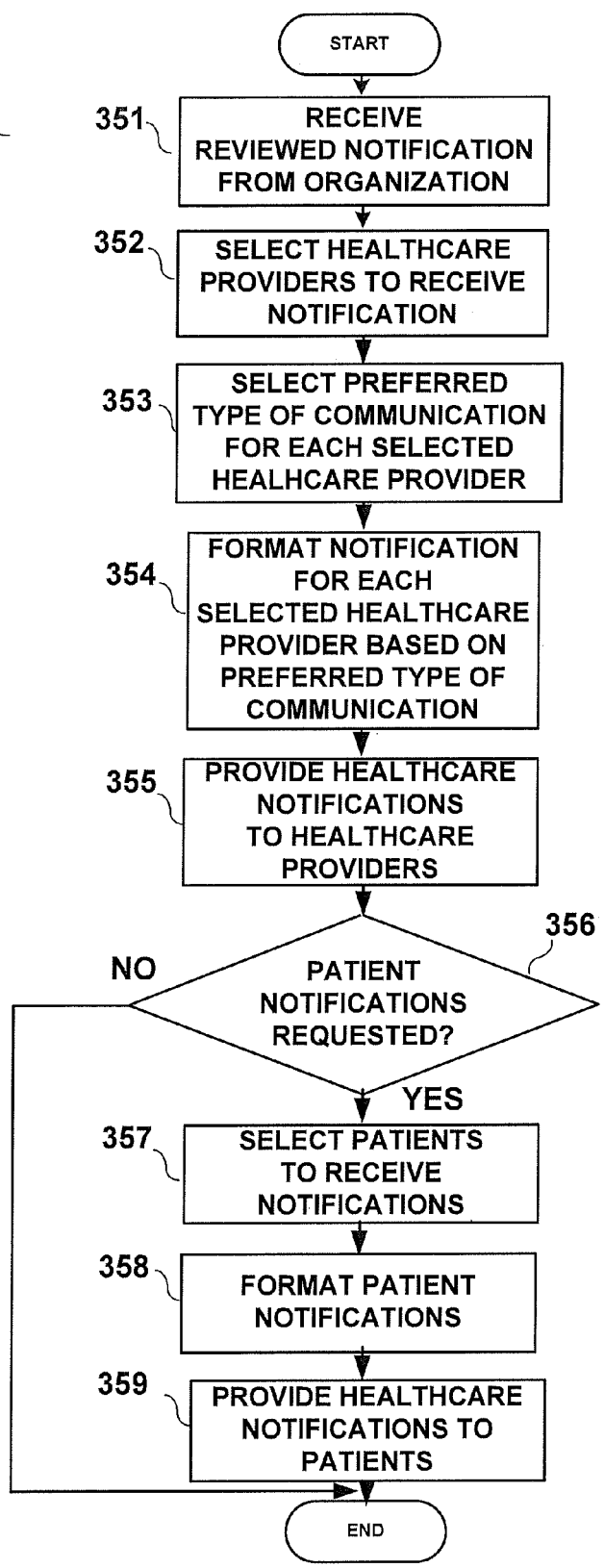

FIG. 3C illustrates a method 350 for providing healthcare notifications to selected healthcare providers based on their preferred mode of communication and then to patients of the healthcare providers. In an embodiment, healthcare website 101 provides healthcare notifications to selected healthcare providers. In an embodiment, method 350 represents an embodiment represented by at least logic blocks 305-309 and 131 shown in FIG. 3A.

Method 350 begins by receiving a reviewed healthcare notification from an organization as illustrated by logic block 351. In an embodiment, the healthcare notification has been reviewed and approved by a reviewing entity. Healthcare providers to receive the notification are selected as illustrated by logic block 352. Healthcare providers to receive the notification may be selected based on a number of criteria that may be stored in a database, such as database 210 shown in FIGS. 2B-C. Healthcare providers may be selected based on their specialty or recently entered or prescribed drugs. Similarly, healthcare providers may be selected based on entered or used medical equipment or medical devices. Also, healthcare providers may be selected based on their entries to a database or answers to queries regarding healthcare notifications.

Logic block 353 illustrates selecting the preferred mode of communication for providing the healthcare notification to the selected healthcare providers. A preferred mode of communication may be email, regular mail, pager, fax, text message or other modes of communication. In an embodiment, healthcare providers enter the preferred mode of communication and profile/contact information at healthcare website 101. In an embodiment, the preferred mode of communication and profile/contact information are obtained from a healthcare provider record stored in database 210.

Figure 6:
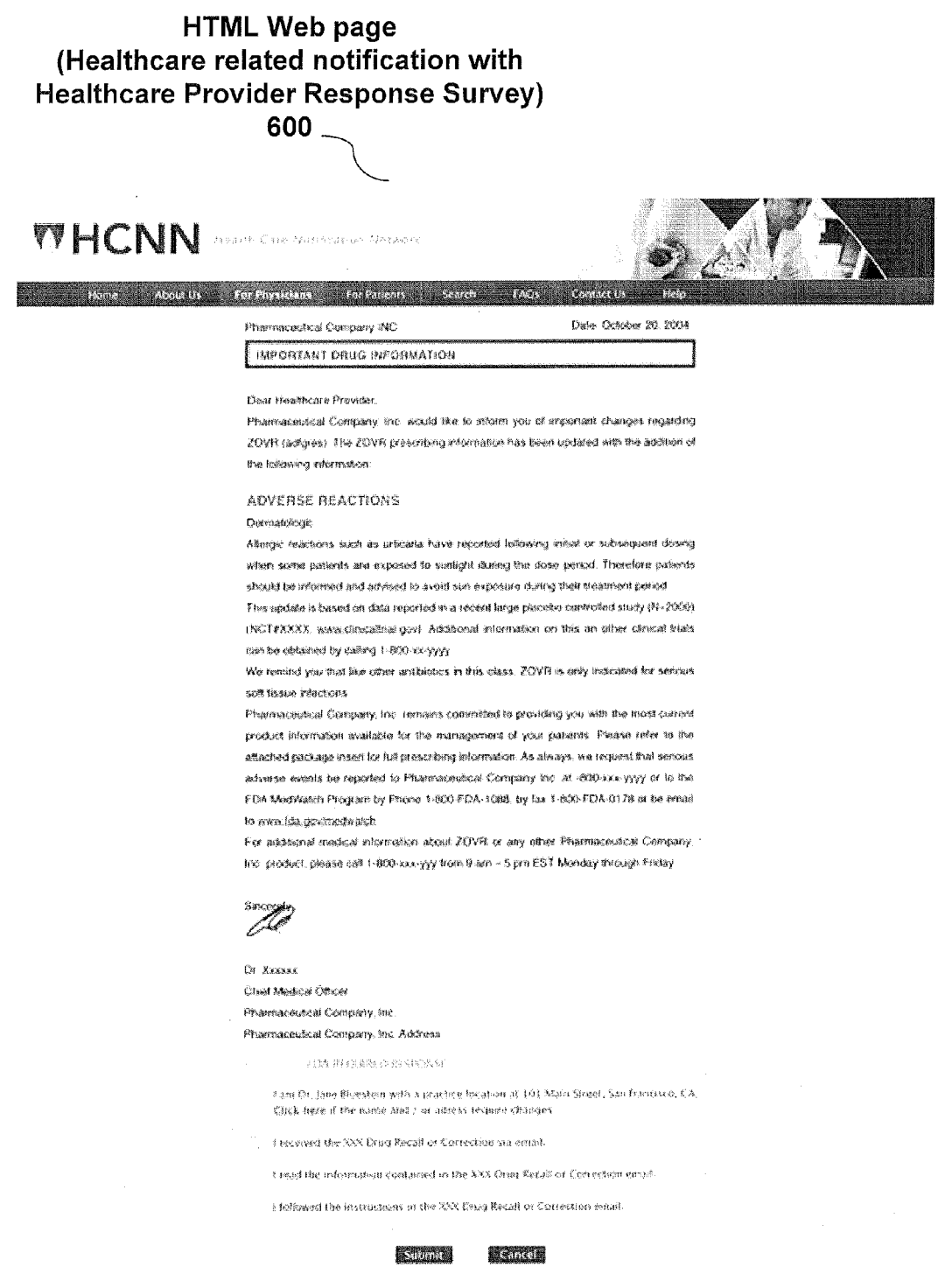

The healthcare notification is then formatted based on the preferred mode of communication and generated to the selected healthcare provider as illustrated in logic blocks 354 and 355. In an embodiment, an email message with a link or URL address to a healthcare notification in a web page at healthcare website 101 is provided to the selected healthcare provider. In embodiments, web pages 500 and 600 as illustrated in FIGS. 5A and 6 are provided. Web page 500 illustrates a notification regarding an allergic reaction of the drug "ZOVR" under certain conditions from a pharmaceutical company Inc. Web page 600 illustrates a similar notification with a "FDA REQUIRED RESPONSE" or survey questions that may be answered and transferred back to healthcare website 101.

In an embodiment, healthcare providers may register for pre-alerts or pre-healthcare related notifications. When system 100 becomes aware that a healthcare notification will be generated shortly, a healthcare provider may receive a pre-alert notice, such as "Healthcare Notification coming tomorrow." These Pre-Alerts or pre-healthcare notifications may be generated to partners, such as medical societies, a day in advance of the healthcare notification. A partner pre-alert may contain both a message to "look for the Alert via the Healthcare Website 101" if the healthcare provider is registered and/or a "register on the Healthcare Website 101 to receive the alert tomorrow" message.

In embodiments, alerts and/or healthcare notifications include a viral marketing message, such as "tell a colleague." In an embodiment, system 100 provides a chat area, as illustrated by logic block 132, where notification recipients can discuss a healthcare notification with colleagues who also received the notification. Similarly, the notification recipient may report adverse reactions or communicate with third parties as illustrated by logic blocks 135 and 136.

A determination, as represented by logic block 356, is made whether the healthcare provider would like to forward a patient version of the healthcare notification to selected patients or all of the healthcare provider patients. When patient notifications are not requested, method 350 ends. Otherwise, control transfers to logic block 357 where patients to receive the patient formatted healthcare notification are selected. In an embodiment, patients may be selected based on previously prescribed medications, health conditions, age or other factors that may be stored in an electronic patient health record in database 210 associated with the healthcare provider.

Patient notifications are then formatted as illustrated by logic block 358 and generated to selected patients as illustrated by logic block 359. In an embodiment, patient healthcare related notification 501, shown in FIG. 5B, is a patient version (or format) of the information in web page 501 that was provided to the healthcare provider (or the healthcare provider's organization—Company ABC Inc.) of the patient. In an embodiment, patient notifications may be emailed. Method 350 then ends.

Figure 3D:
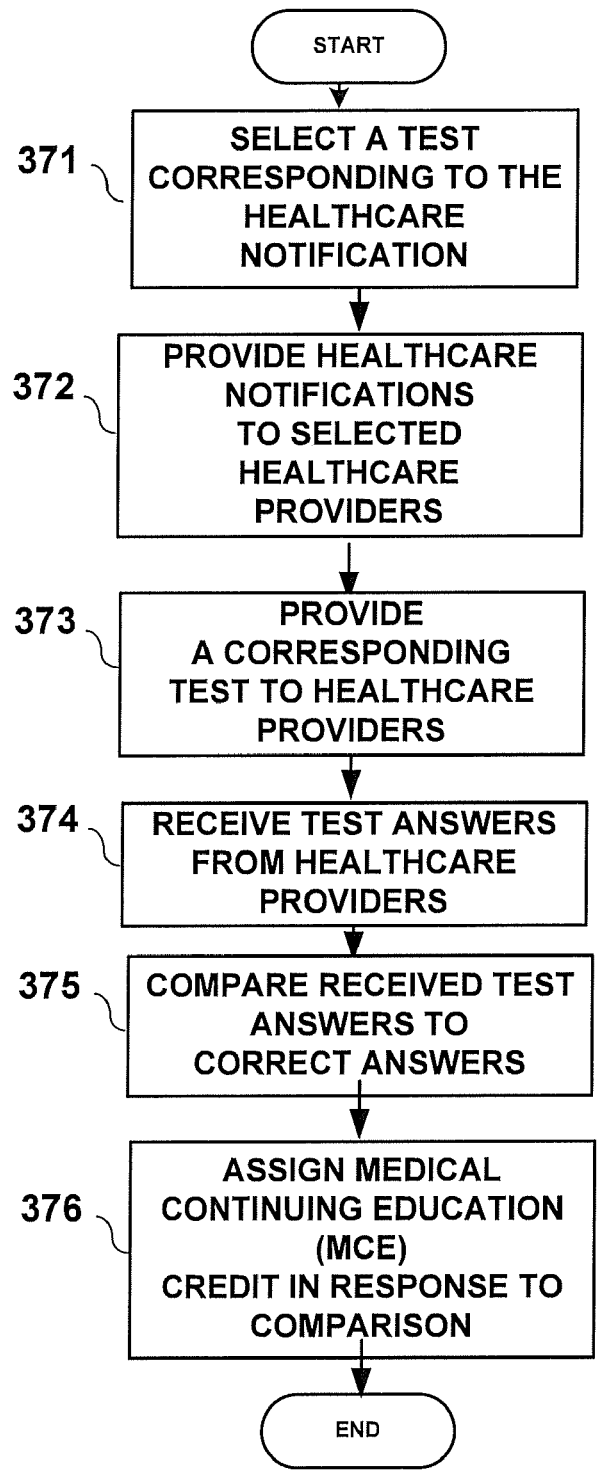

FIG. 3D illustrates a method 370 for providing CME information, such as associated CME tests, with healthcare notification that are provided to healthcare providers. In an embodiment, healthcare website 101 provides healthcare notifications and CME information to selected healthcare providers. In an embodiment, method 370 represents an embodiment represented by at least logic blocks 305-309 and 139 shown in FIG. 3A-B.

Figure 11:
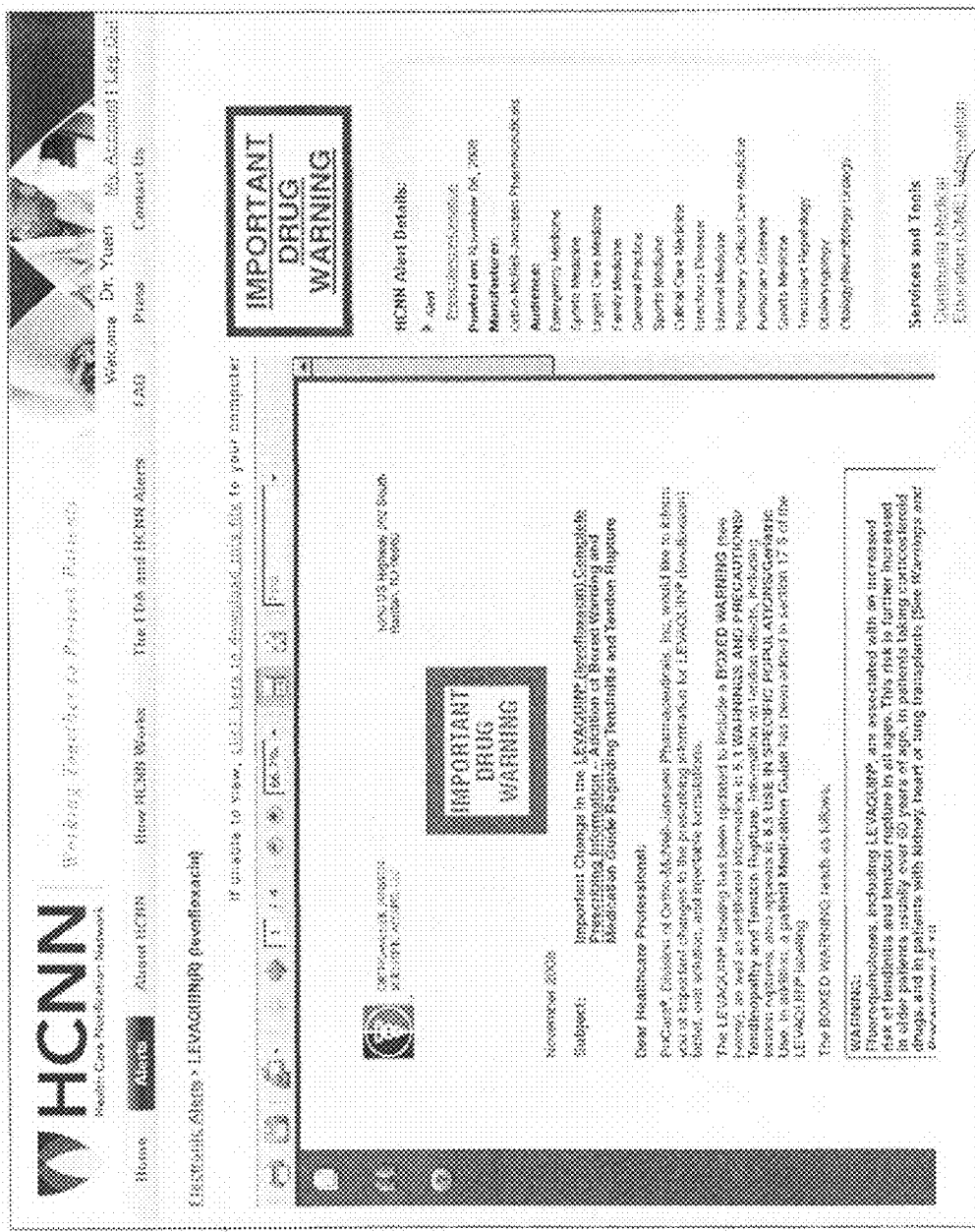
FIG. 11 illustrates an exemplary HTML web page 1100 that provides a healthcare related notification that includes a link 1101 to Continuing Medical Education ("CME") information.
Figure 12:
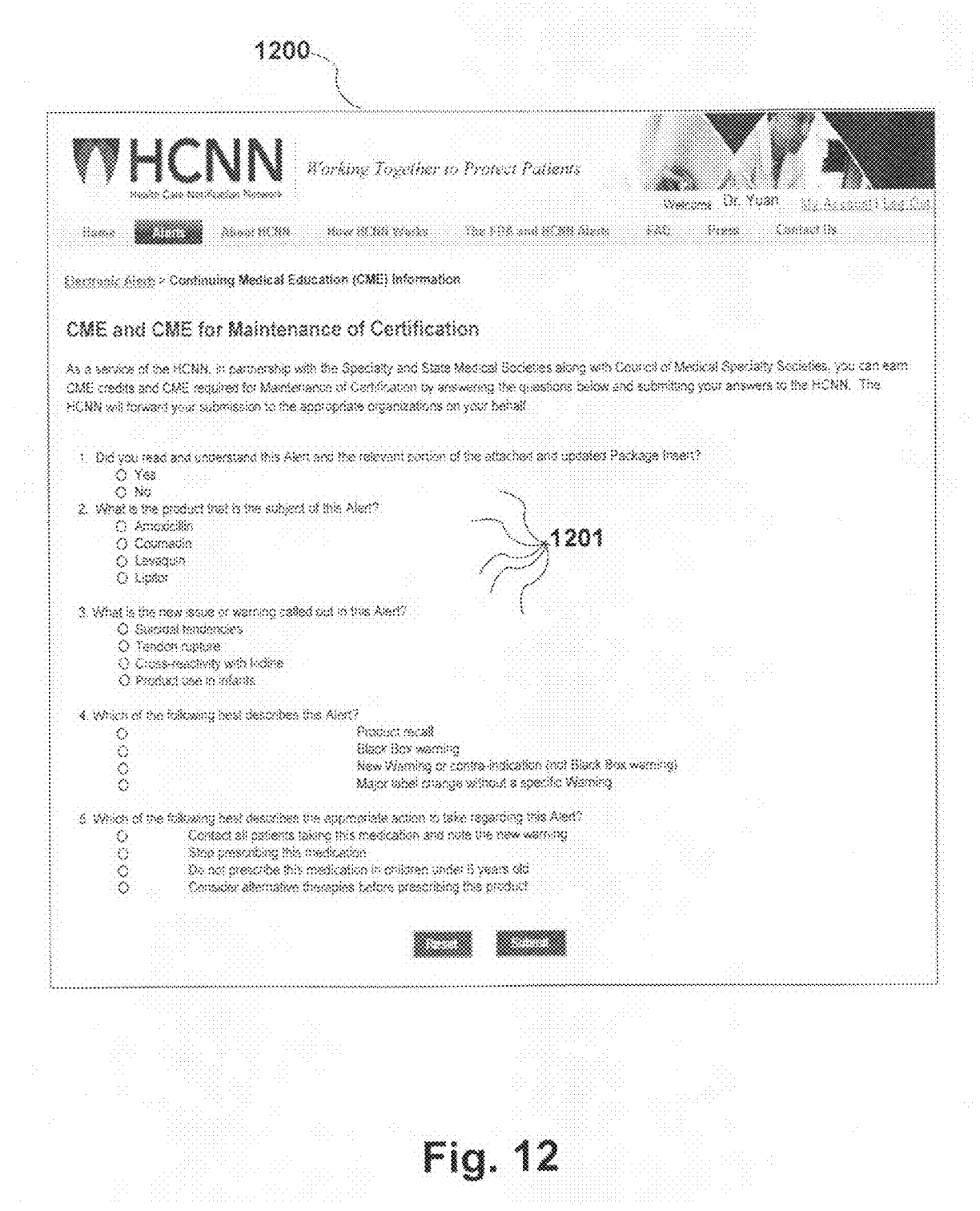

Method 370 begins by selecting a CME test corresponding to a particular healthcare notification to be provided to a selected number of healthcare providers as illustrated by logic block 371. In an embodiment, a CME test for a particular healthcare notification is obtained from healthcare notification record 210b in database 210 shown in FIG. 2C. In an embodiment, the CME test includes questions regarding an associated healthcare notification to be provided. For example, "Test 3" is selected for "Notification 3" that has a notification that relates to "internal" medicine. In another example, FIG. 11 illustrates a web page 1100 including a healthcare notification regarding a drug ("LEVAQUIN") warning and FIG. 12 illustrates a web page 1200 including CME questions 1201 regarding the content of the drug warning in FIG. 11. In alternate embodiments, a CME test may be selected not on a specialty but on types of drugs prescribed, medical devices used and/or answers to registration questions, singly or in combination.

Logic block 372 illustrates providing healthcare notifications to selected healthcare providers. For example, an email 1000 including a link 1001 to a healthcare notification is provided to "Dr. Yuan," along with other selected healthcare providers, from website 101 via one or more healthcare provider processing device 104a. In an embodiment, link 1001 may be clicked-on by a healthcare provider to access the healthcare notification shown in FIG. 11. If the link does not work, an URL address 1002 for a web browser is provided.

Logic block 373 illustrates providing a CME test corresponding to the healthcare notification. For example, link 1101 in web page 1100 shown in FIG. 11 may be "clicked-on" to access a CME test, such as questions 1201 shown in FIG. 12. For example, questions 1201 cover the subject matter of the drug warning shown in web page 1100. A question may include a multiple choice question such as "what is the product that is the subject of the Alert?"

After receiving the CME test, a healthcare provider may answer the questions and click-on the "submit" button that transfers the answers back to website 101 as illustrated by logic block 374.

Logic block 375 illustrates comparing the received CME test answers with the correct answers stored in record 210b in database 210 by content management software component 203.

Logic block 376 then assigns and stores earned CME credits in "Total Continuing Medical Education Credits Earned" to corresponding healthcare providers in profiles 210a of database 210. For example, Physician Fotsch has earned "100" CME credits. Healthcare providers are then able to view the earned credits by way of healthcare website 101. The use of CME information with healthcare notification provides an unexpected result. Healthcare notifications can be provided to healthcare providers in a timely and efficient manner and at the same time allow the healthcare provider to earn CME credits without requiring additional research and time in obtain necessary CME credits. The opportunity of obtaining CME credits with healthcare notifications allows healthcare providers to address CME and Maintenance of Certification (MOC) requirements for patient safety education and also provides an incentive for the healthcare provider to access important healthcare notifications.

Figure 3E:
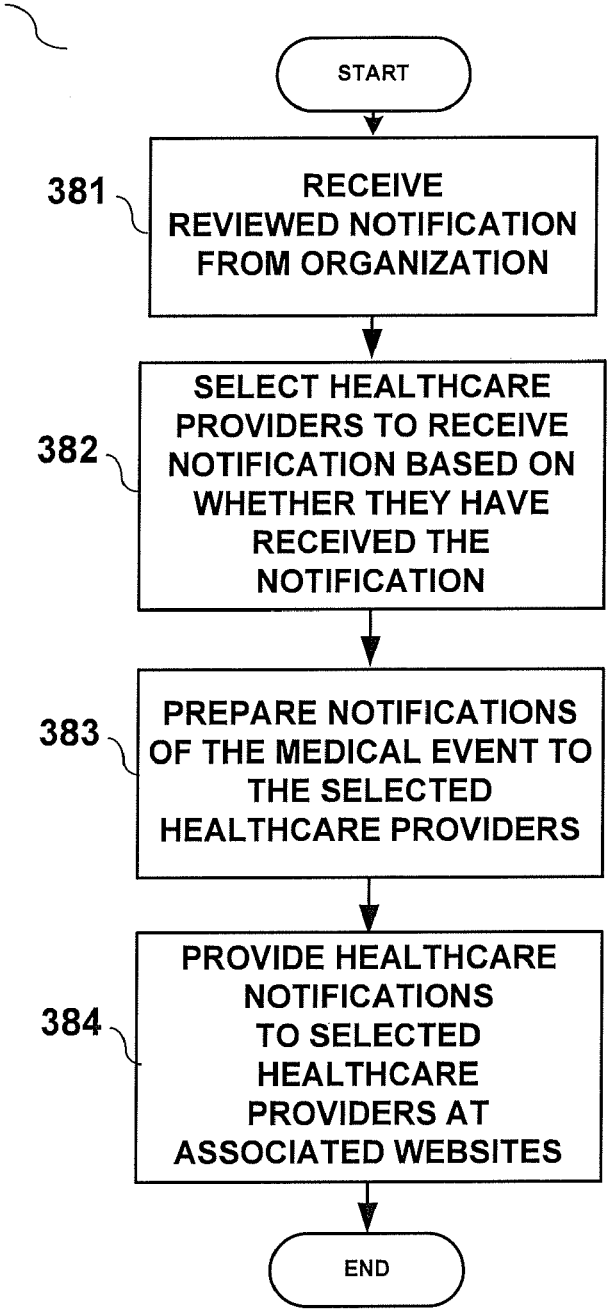

FIG. 3E illustrates a method 380 for providing healthcare notifications that are provided to healthcare providers by way of associated healthcare websites. In an embodiment, healthcare website 101 provides healthcare notifications to selected healthcare providers by way of associated healthcare website 151. In an embodiment, method 380 represents an embodiment represented by at least logic blocks 305-309 shown in FIG. 3A.

Method 350 begins by receiving a reviewed notification from an organization as illustrated by logic block 381 and similar to the description above in regard to logic block 351.

Logic block 382 then illustrates selecting particular healthcare providers that will receive the healthcare notification at associated healthcare websites. In an embodiment, the selection of healthcare providers to receive a healthcare notification at an associated healthcare website is determined as described herein and based at least in part on whether the healthcare provider has already received and acknowledged the healthcare notification (i.e. the healthcare provider has received and acknowledged an email). Also, a selection will be based on whether the selected healthcare provider is a member or registered with a particular associated healthcare website. In an embodiment, Content Management 203 (shown in FIG. 2A) will determine what healthcare notification in record 210b will be provided to a particular set of healthcare providers in profiles 210a in database 210 of FIG. 2C (i.e. determined based on specialty). Content Management 203 then may also determine whether the healthcare providers in the selected set have already received the notification and/or are members of the associated healthcare websites as indicated in profiles 210a. For example, profiles 210a show that "Physician Del Guidice" has not received/acknowledged "notification 2" (indicated by "N" for no in FIG. 2C) and is a member of the associated electronic prescription (ERX) website. Therefore, "Dr. Del Guidice" would be selected to provide a healthcare notification (i.e. related to "radiology" because of her specialty) at the electronic prescription website.

Figure 13:
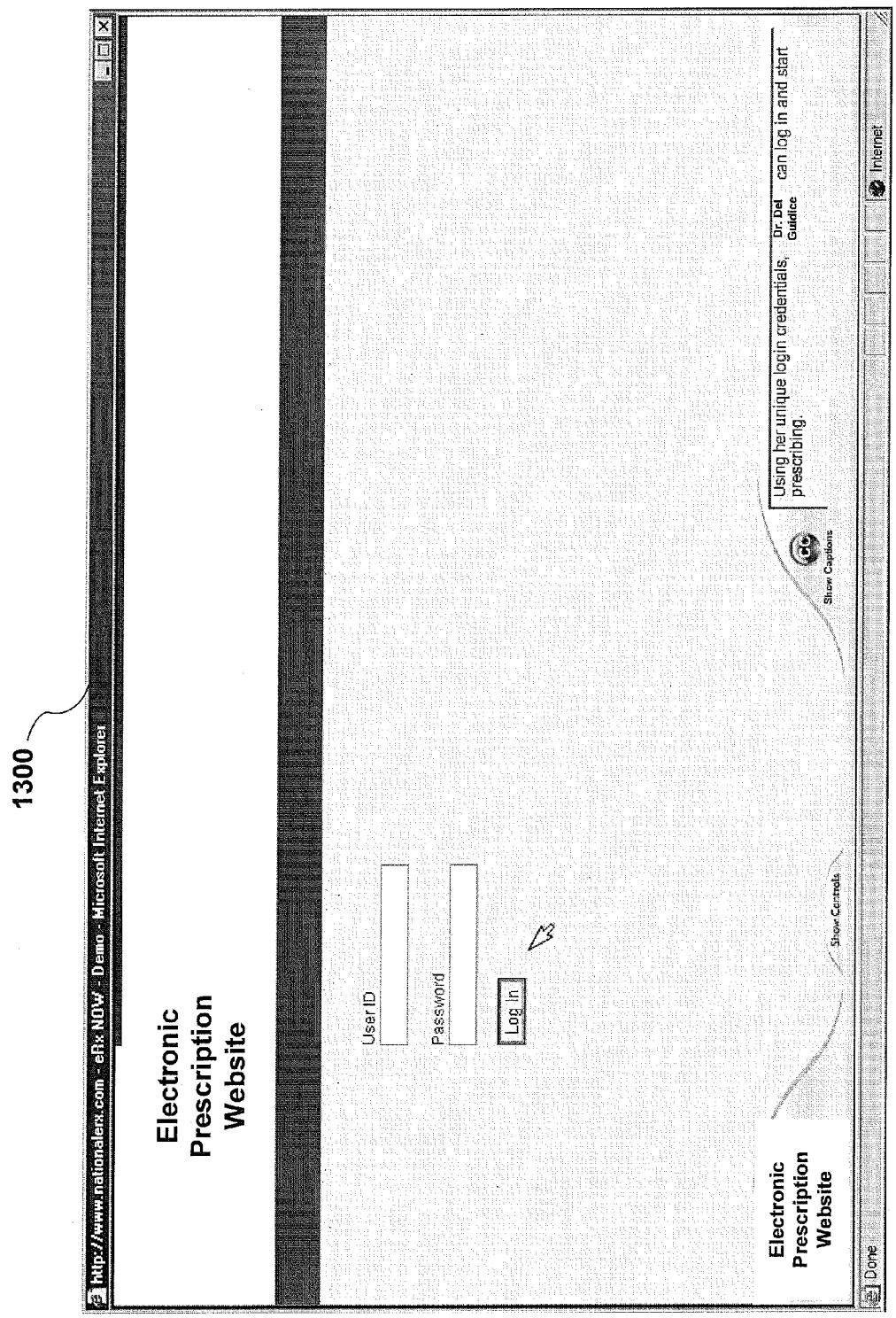
FIG. 13 illustrates an exemplary HTML web page 1300 that provides a log in function to an electronic prescription website.
Figure 14:
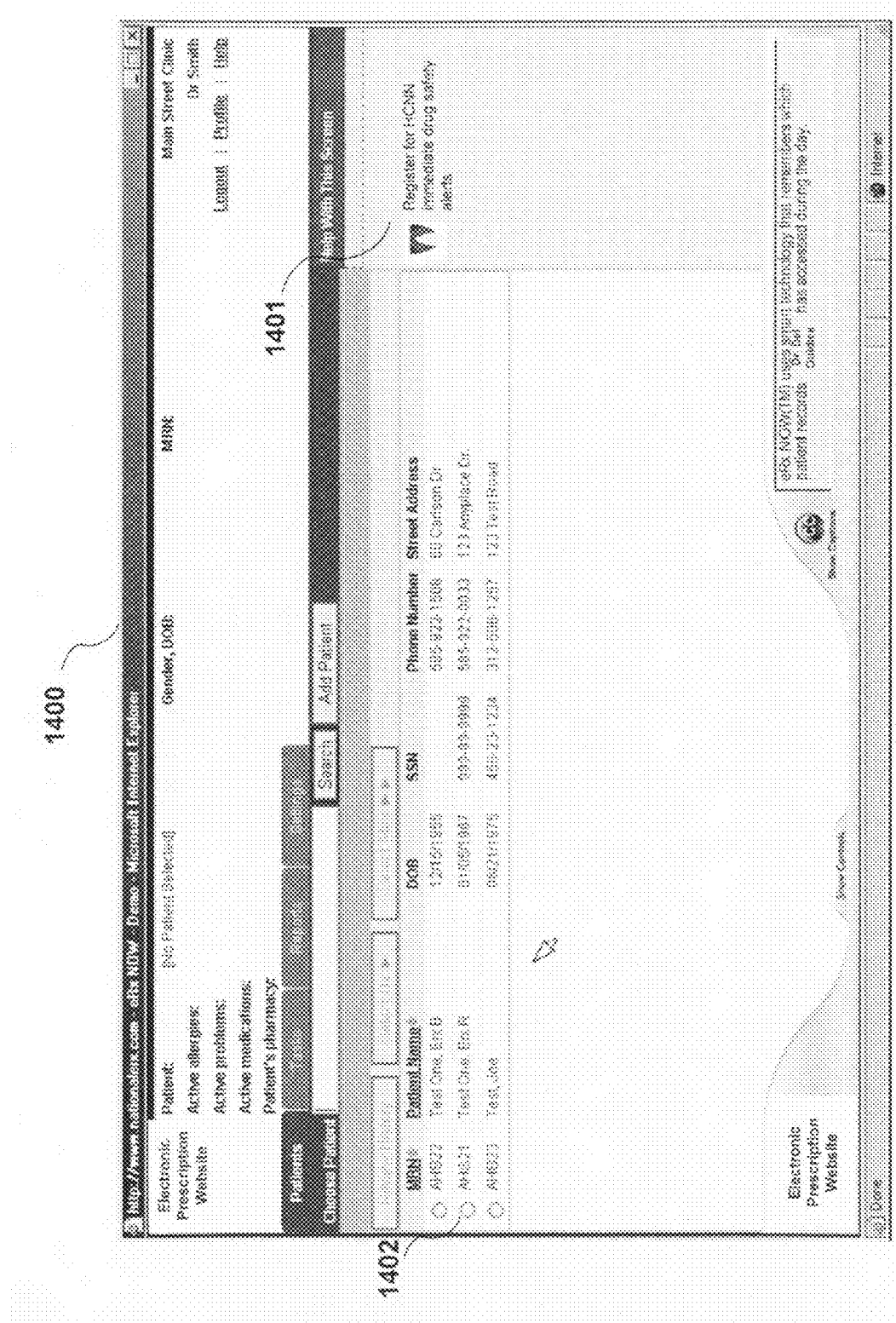
FIG. 14 illustrates an exemplary HTML web page 1400 provided by the electronic prescription website that enables registration for healthcare related notifications.
Figure 15:
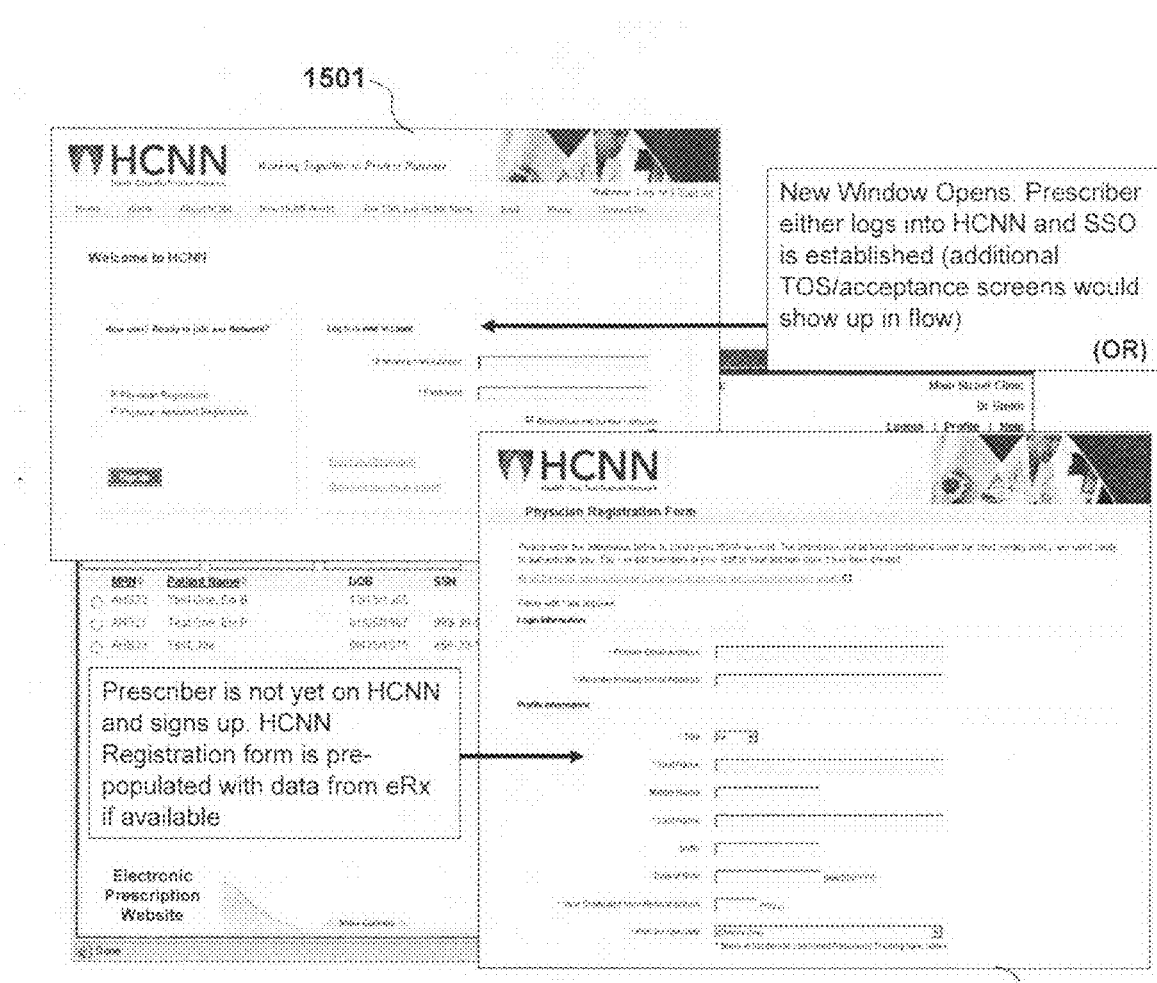
FIG. 15 illustrates exemplary HTML web pages 1501-1502 used to log in or register for healthcare related notifications at a healthcare website.

Logic block 383 illustrates the preparation of the healthcare notifications for the selected healthcare providers at the associated healthcare websites. In an embodiment, a healthcare notification may be provided at an associated healthcare website by a link to register at healthcare website 101 as illustrated by link 1401 in web page 1400 at the electronic prescription website. Before reaching web page 1400 a healthcare provider would log into the electronic prescription website by providing the appropriate "username" and "password" as shown by web page 1300 in FIG. 13. After a healthcare provider clicks-on link 1401, either web pages 1501 or 1502 shown in FIG. 15 may be provided in embodiments. If the healthcare provider is already registered with healthcare website 101, web page 1501 is provided and allows for the healthcare provider to log-in and obtain the healthcare notification. If the healthcare provider is not registered with healthcare website 101, web page 1502 is provided for registration and subsequent viewing of the healthcare notification.

Figure 16:
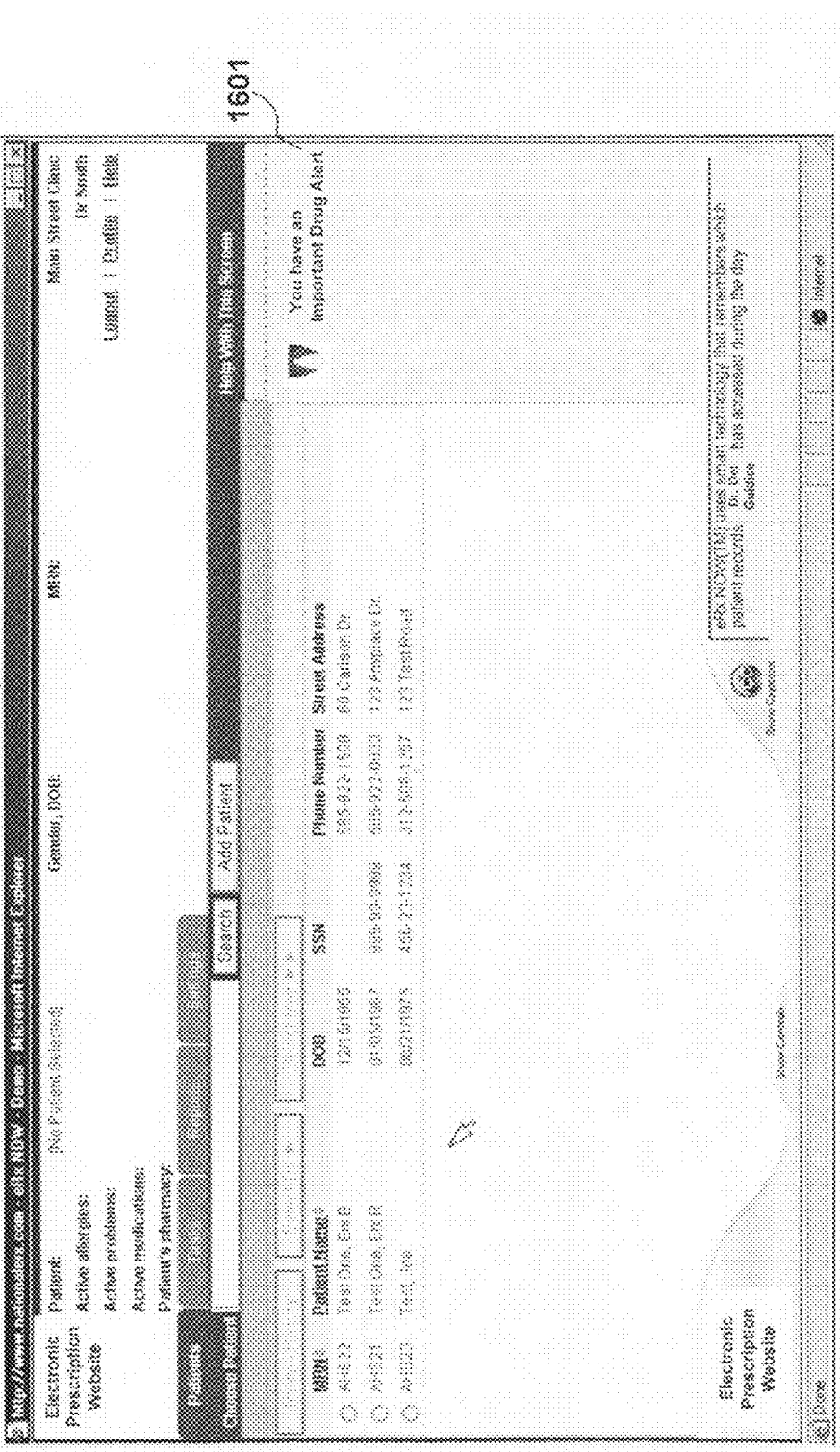
FIG. 16 illustrates an exemplary HTML web page 1600 provided by the electronic prescription website that includes a link to a healthcare related notification.
Figure 17:
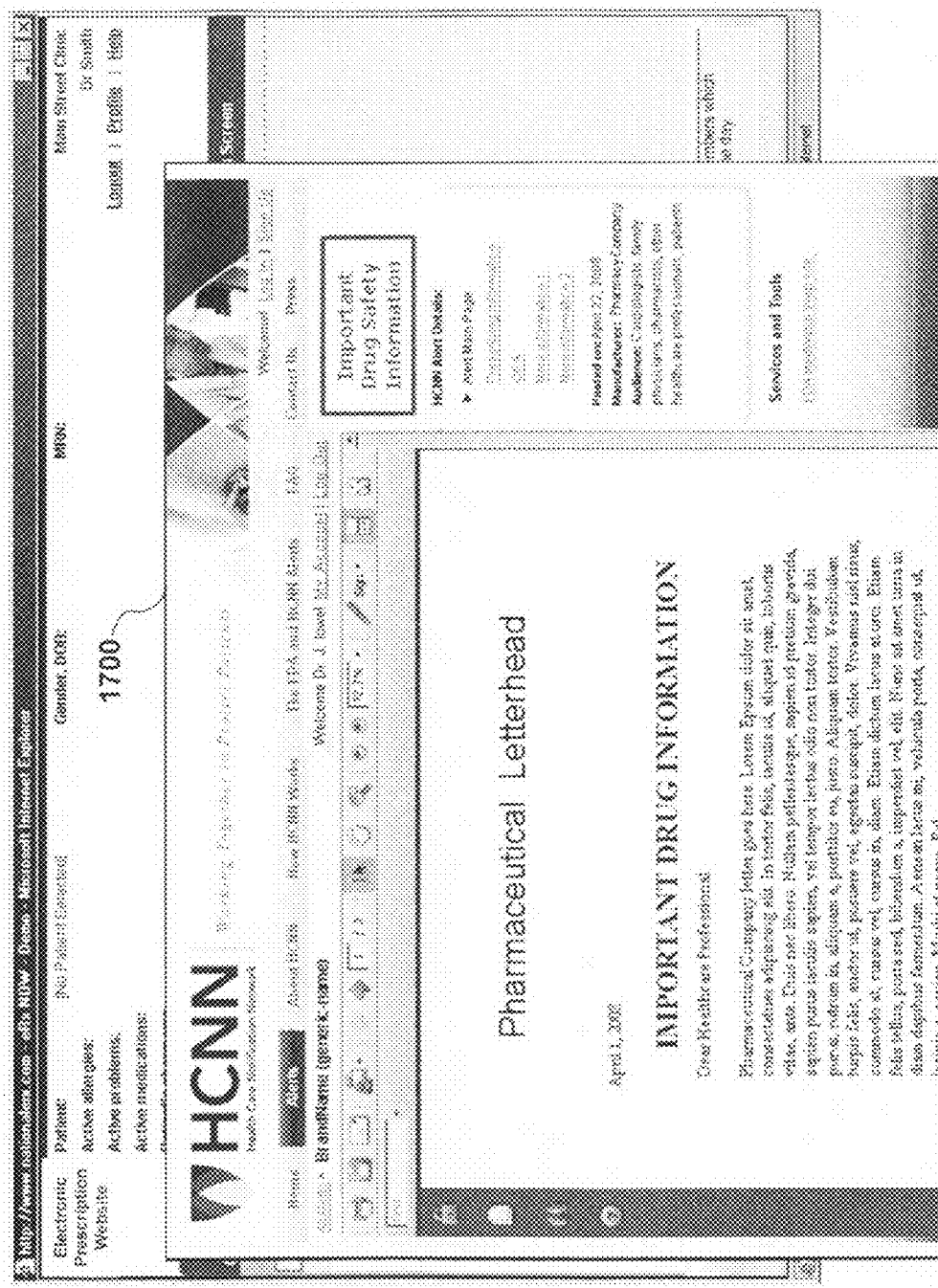
FIG. 17 illustrates an exemplary HTML web page 1700 including healthcare related information that is accessed through a link at the electronic prescription website.
Figure 18:
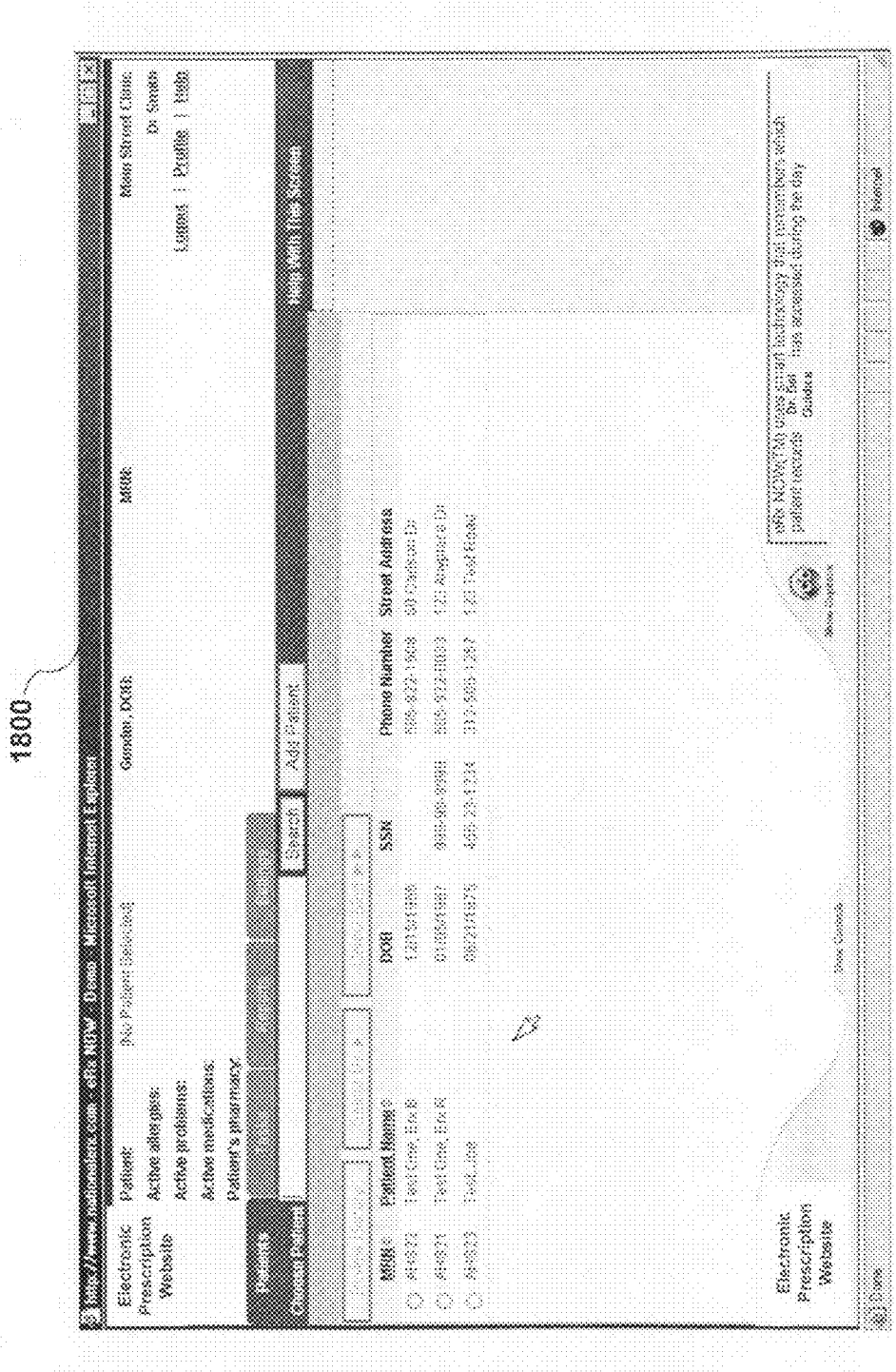
FIG. 18 illustrates an exemplary HTML web page 1800 provided by the electronic prescription website that does not indicate that healthcare related notifications are available as the healthcare related notification has been viewed.

Logic block 384 illustrates providing the healthcare notification to the selected healthcare providers by way of the associated healthcare website. In an embodiment, healthcare notifications are posted at the healthcare website 101 and are accessed after registration or sign-on of the healthcare provider at the associated healthcare website described above. In an alternate embodiment, an indication of a healthcare notification in the form of a link at an associated web page is provided. For example, link 1601 indicating "You have an Important Drug Alert" is provided at a web page 1600 shown in FIG. 16 of a selected healthcare provider at the electronic prescription website. The healthcare provider then may click-on link 1601 to view the healthcare notification on web page 1700 at healthcare website 101 through a new browser window as shown in FIG. 17. In an embodiment, a link is not provided as shown in FIG. 18 if the selected healthcare provider had already viewed the selected healthcare notification or received/acknowledged the healthcare notification provided by email.

Figure 3F:
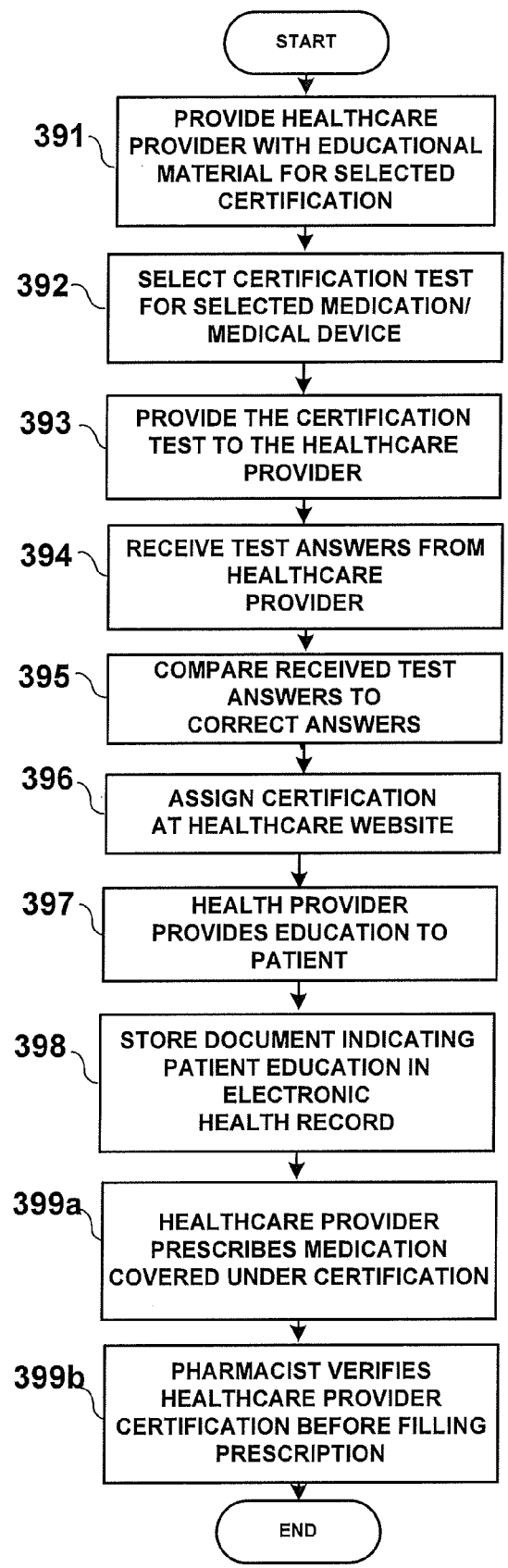

FIG. 3F illustrates a method 390 for providing a certificate to a healthcare provider and verifying such certification by way of a healthcare website 101. In an embodiment, method 390 represents an embodiment represented by at least logic blocks 305-309 and 140 shown in FIGS. 3A-B. A delivery agent, such as a pharmacist and/or medical device manufacturer, is able to verify that a healthcare provider has been certified for prescribing a particular medication or using a particular medical device before filling a prescription for a patient or providing a medical device to the healthcare provider for the patient. For example, delivery agent 171 may access healthcare website 101 by way of delivery agent processing device 172 and Internet 103 to verify certification(s) of healthcare provider(s) 120 before delivering a medication and/or medical device to a patient (or to a healthcare provider for use with a patient).

In an embodiment, method 390 begins by providing a selected healthcare provider with information to obtain a certificate for a particular medication and/or medical device as illustrated by logic block 391. In an embodiment, an electronic healthcare notification as described herein may include or attach information for obtaining a certification. For example, an electronic healthcare notification regarding a medical event may include educational material or a link to the educational material at healthcare website 101 to be reviewed before passing a test necessary for certification. In an embodiment, healthcare providers are selected to obtain the information regarding certification similar to being selected for an electronic healthcare notification. In an embodiment, Content Management 203 (shown in FIG. 2A) queries record 210a (shown in FIG. 2C) to determine a healthcare provider's specialty and/or possible medications (drugs) and/or medical devices (such as equipment) used. When Content Management 203 determines that a healthcare provider is to receive an electronic healthcare notification, a determination is also made by Content Management 203 whether a certification is required for the particular medication/medical device covered by the electronic notification in record 210a. For example, record 210a illustrates that Physician "Fotsch" has received certification in prescribing "Lidocaine" while Physician "Choy" has not received certification in prescribing "Tacrine."

In an alternate embodiment illustrated by logic block 391, education material for certification or a link to education material is not provided with an electronic healthcare notification regarding a medical event and is included in periodic electronic communications, such as e-mails, to selected healthcare providers based on specialty and/or medications prescribed and/or medical devices used as well as whether the healthcare provider is already certified. In still another embodiment, logic block 391 represents healthcare providers receiving educational material or notifications regarding required certifications by registering or logging into healthcare website 101.

Logic block 392 illustrates selecting a certification test corresponding to a particular medication or medical device. In an embodiment, a certification test for a particular medication/medical device is obtained from healthcare record 210c in database 210 shown in FIG. 2C. In an embodiment, the certification test includes questions regarding a particular medication/medical device is be provided. For example, "Test 3" is selected for certification to prescribe the medication "Tacrine." In an embodiment, the form of questions for certification is similar to the form of questions shown in FIG. 12.

Logic block 393 illustrates providing a certificate test in electronic form. The certificate test may correspond to a healthcare notification or may be accessed directly from the healthcare website 101.

After receiving the certificate test, a healthcare provider may answer the certification questions and transfer the answers back to website 101 as illustrated by logic block 394.

Logic block 395 illustrates comparing the received certification answers with the correct answers stored in record 210c in database 210 by content management software component 203.

Logic block 396 then assigns and stores a certificate (or representation thereof) for a medication/medical device to a corresponding healthcare provider in record 210a of database 210. For example, Physician Fotsch has earned certifications for medication/medical devices illustrated by the numbers 1, 2 and 4 while Physician Del Guidice has earned certifications for medication/medical devices illustrated by the numbers 1 and 3.

In an embodiment, a patient is also educated as illustrated by logic block 397. In an embodiment, a healthcare provider educates the patient regarding the particular medication and/or medical device that may include side effects and associated risks.

Logic block 398 illustrates documenting the education of the patient regarding the medication and/or medical device. In an embodiment, a document that describes the medication and/or medical device including its side effects and risks is signed by the patient and stored in the patient's medical records, such as an electronic medical record. The patient electronic medical record may be stored at healthcare website 101 or at an associated web site. The document indicates that the patient has read, understood, and accepted the risks and side effects associated with the medication/medical device. In an embodiment, healthcare website 101 stores an indication that such a document exists even though the document may not be stored at healthcare website 101. In an embodiment, an indication that a particular patient has been educated for a particular medication/medical device or certified (via the stored document) may be stored in database 210 that may be accessed by way of website 101.

Logic block 399a illustrates a healthcare provider prescribing a medication and/or ordering a medical device that requires certification. In various embodiments, the prescription and/or order of a medical device may be provided electronically. In an embodiment, healthcare provider(s) 120 prescribes a medication to patient(s) 108 for a medication that requires a certificate. In an alternate embodiment, healthcare provider(s) 120 order a medical device from a medical device manufacturer. Patient (s) 108 then may provide the prescription to a pharmacist, or similar delivery agent.

A pharmacist, or other delivery agent, then verifies that healthcare provider(s) 120 is certified for prescribing the prescribed medication as illustrated by logic block 399b. In an embodiment, a delivery agent 171 logs into healthcare website 101 via delivery agent processing device 172 in order to verify that healthcare provider(s) 120 is certified. In an alternate embodiment, delivery agent 171 also verifies that the patient is likewise certified or has been educated as illustrated in logic block 399b. After the verification, the delivery agent provides the medication to the patient or the medical device to the healthcare provider as illustrated by logic block 399b.

Figure 3G:
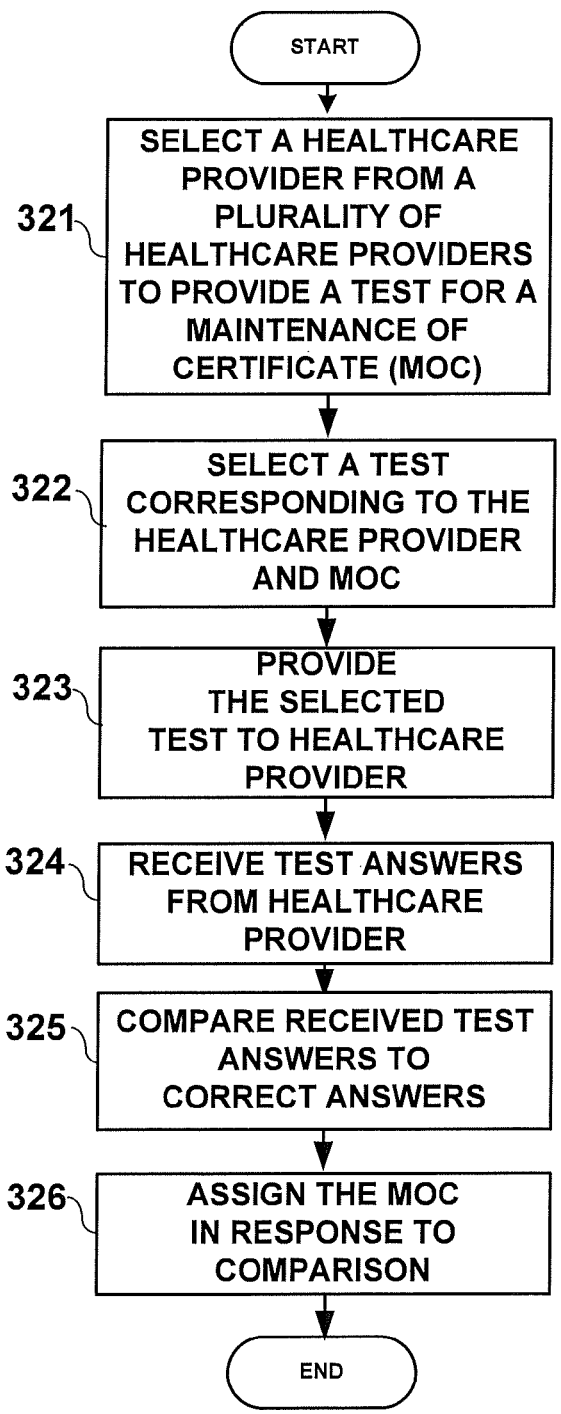

FIG. 3G illustrates method 320 for providing MOCs to healthcare providers. In an embodiment, method 320 represents an embodiment represented by at least logic blocks 305-309 and 141 shown in FIGS. 3A-B.

Method 320 begins by selecting a healthcare provider from a plurality of healthcare providers to provide a test for obtaining a MOC as illustrated by logic block 321. In an embodiment, the MOC test is included or attached to healthcare notification to be received by the healthcare provider. In an embodiment, the healthcare provider is selected based on a specialty stored in record 210a. In another embodiment, the healthcare provider is selected based on other criteria, such as the date of completion of the previous MOC and/or whether other steps required for a MOC have been completed. Information regarding status/completion of MOC requirements or steps (MOC information) may be stored in record 210a and accessed by healthcare providers and others by way of healthcare website 101 in embodiments.

A MOC test corresponding to a particular healthcare provider is selected as illustrated by logic block 322. In an embodiment, a MOC test for a particular healthcare provider is obtained from record 210d in database 210 shown in FIG. 2C. In an embodiment, a MOC test is selected based on the specialty of the healthcare provider.

Logic block 323 illustrates providing a MOC test corresponding to the healthcare provider. In embodiments, the MOC test may be provided in electronic form, by way of a link in an e-mail and/or from a web page in healthcare website 101.

After receiving the MOC test, a healthcare provider may answer the MOC questions and submit the answers to healthcare website 101 as illustrated by logic block 324.

Logic block 325 illustrates comparing the received MOC answers with the correct MOC answers stored in record 210d in database 210 by content management software component 203.

When the MOC test is successfully passed, logic block 326 then assigns and stores such indication in record 210a in database 210. For example, Physician Fotsch's MOC is current and the requirements that were completed are stored in a MOC information field of record 210a.

III. SOFTWARE ARCHITECTURE

FIG. 2A illustrates software components of software 102a that may be executed on healthcare platform processing device 102, shown in FIGS. 1A-C, to provide healthcare website 101 including other healthcare related services. In an embodiment, healthcare platform software 102a includes machine/computer readable or executable instructions. In an embodiment, software 102a is stored in an article of manufacture, such as a computer readable medium that may be removable from or included in a processing device. For example, software 102 may be stored in a magnetic hard disk, an optical disk, a floppy disk, CD-ROM (Compact Disk Read-Only Memory) as illustrated in FIG. 1, RAM (Random Access Memory), ROM (Read-Only Memory), EEPROM (Electrically Erasable Programmable Read-Only Memory) or other readable or writeable data storage technologies, singly or in combination. In alternate embodiments, software 102a may be transferred by an electronic signal or downloaded by way of the Internet using wired and/or wireless connections.

In embodiments, FIG. 2A illustrates software components that may include a software program, software object, software function, software subroutine, software method, software instance or a code fragment, singly or in combination. In embodiments, software components illustrated in FIG. 2A have functions described in detail below.

A. Healthcare Portal 200

Healthcare portal 200 provides content consumers, such as healthcare providers, government agencies, medical boards, medical societies, pharmaceutical manufacturers, medical device manufacturers, etc., with access to medical event information that includes medication recalls and warnings, medical device recalls and warnings, medical equipment recalls and warnings. In particular, Healthcare portal 200 displays 1) most recent recall and warning information for medicines, medical devices and medical equipment; 2) most viewed recall and warning information; 3) specific recall data and ancillary materials including reach media data (from rich media 209 described below) such as photos and video and or suggested communications to patients; and 4) search and list data via various combinations of search criteria. For example, a user will be able to enter various search criteria, such as manufacturer name, type of recall, product name, etc., to obtain a healthcare notification from an internal search software component.

Healthcare portal 200 also provides content consumers with: 1) access to healthcare news and publications; 2) connectivity to selected content providers, such as pharmaceutical companies, manufacturers, and government organization such as the FDA (in an embodiment IC 205 described below is used to provide this service); 3) a report function of adverse reaction to a medicine; 4) order drug samples; 5) order brochures; 6) access to maintenance functions such as maintaining healthcare provider profiles/contact information; 7) access to targeted search of information within the portal and through external search engines; 8) connectivity to external applications, such as secure messaging communication with healthcare providers, social networks related or dedicated to healthcare content and discussion forums dedicated or related to healthcare content (in an embodiment IC 205 described below is used to provide this service); 9) provide tests (along with electronic notifications) for CME credits as well as access to earned CME credit totals; 10) provide status of requirements to satisfy MOC as well as providing MOC tests for particular healthcare providers; and 11) provide certificates to healthcare providers to prescribe particular medications and/or use particular medical devices after successful passing provided tests.

B. Email and Mobile Alert and Notification 201/202

Email and Mobile Alert and Notification 201/202 provides content consumers with real time notifications associated with release of healthcare related information, such as medication recalls and warnings, medical device recalls and warnings, and medical equipment recalls and warnings.

In embodiments, notifications may be delivered to predetermined healthcare providers via a variety of electronic mediums, such as emails, facsimile, SMS messages, IM messages, pager calls or an equivalent. The electronic notifications may be sent at a predetermined time as selected by the organization or a specific end user.

In embodiments, notifications may contain detailed information, brief information or just a pointer (or link) to information which can be accessed via healthcare website 101.

C. Content Management 203

Content Management (CM) 203 provides content contributors with ability to publish content associated with release of healthcare notifications, such as medication recalls and warnings, medical device recalls and warnings, and medical equipment recalls and warnings.

CM 203 also enables monitoring appropriate use of healthcare website 101 by content providers. In an embodiment, CM 203 is responsible for providing CME service 139 and in particular selecting CME tests corresponding to healthcare notifications. In addition, CM 203 may compare received CME test answers with correct answers to assign and record CME credits. Similarly, CM 203 is responsible for certification service 140 and MOC service 141. CM 203 selects a particular educational material and test to be passed to a particular certificate and/or MOC. CM 203 also compares certificate and MOC test answers with correct answers to assign and store certificates and MOC test results. CM 203 may also be responsible for recording the status of other MOC requirements. In an embodiment, CM 203 may initiate the transfer of a selected MOC test to selected healthcare providers based on the healthcare provider's specialty and/or the previous MOC completion date.

D. Reporting and Business Intelligence 204

Reporting and Business Intelligence (RBI) 204 provides content providers with a variety of data associated with release and receipt of healthcare information, such as medication recalls and warnings, medical device recalls and warnings, and medical equipment recalls and warnings. In an embodiment, RBI 204 provides a report to organizations of healthcare providers who have received notifications and answers to survey questions.

Reports provided by RBI 204 are delivered based on roles and data access rules maintained by user management 207 described below.

E. Integration and Connectivity 205

Integration and Connectivity (IC) 205 provide external parties with connectivity to healthcare website 101. Connectivity to external parties is bidirectional, meaning that external parties can submit and retrieve data from healthcare website 101. Both submission and retrieval of the data is controlled through multilayer security ensuring that only authorized parties can access information. In an embodiment, IC 205 provides communication with associated healthcare websites by way of applets and/or portlets. In an embodiment, IC 205 allows for a single sign-on ("SSO") at associated healthcare website 151 that allows access to healthcare website 101.

F. Member Services 206

Member Services 206 enables healthcare website 101 support and customer service staff to perform operations that require accessing or altering data. In particular, Member Services 206 is used to provide minor technical support to the content providers and content consumers, such as restoring lost passwords and user IDs.

G. User Management 207

User Management 207 stores information associated with content consumers and content providers as well as the associated permissions, roles and access rights.

H. Support 208

Support 208 maintains a safe and secure operation of healthcare website 101. With security, privacy and safety being complex multi-fold objectives, Support 208 includes a number of software components serving multiple objectives: logging and auditing, internal alert and notification, performance and availability control.

I. Rich Media 209

Rich Media 209 stores and provides photos, audio, large documents and video and/or suggested communications to patients in regard to healthcare notifications.

J. Centralized Database 210

Central database 210 stores and maintains information such as recall data, notification information and application metadata or information that describes the composition and architecture of data. For example, metadata may include a data dictionary. Most software components illustrated in FIG. 2A access central database 210.

FIG. 2B illustrates healthcare provider profiles/records 210a that includes a plurality of healthcare provider profiles and preferred electronic notification contact information. FIG. 2B illustrates a portion of a data structure stored in database 210 and one of ordinary skill in the art understands that database 210 includes other data as well. Healthcare provider profile 210a includes fields of information associated with each healthcare provider name or physician. In particular, each physician name has an associated 1) medical specialty; 2) typically prescribed or currently prescribed drugs and typically used equipment or currently used equipment; 3) preferred type of electronic notification; 4) contact address; and 5) default or address that the notification may be mailed. One of ordinary skill in the art also understands that healthcare provider profiles 210a may include more or less fields of information depending upon a particular embodiment.

In an embodiment illustrated in FIG. 2C, database 210 includes healthcare provider profiles 210a that include 1) certifications received for medications and medical devices, 2) MOC status, 3) MOC information, 3) total continuing medical education (CME) credits earned by the healthcare provider, 4) which healthcare notification has been received/acknowledged by the healthcare provider (Yes-Y, No-N) and 5) which associated healthcare websites (ERX, EHR, etc.) does the healthcare provider belong to (Yes-Y, No-N).

In an embodiment, CM 203 software component accesses healthcare provider profiles 210a to select which healthcare provider will receive a healthcare related electronic notification in response to healthcare notification from an organization, such as a drug manufacturer. In an embodiment, user management 207 and CM 203 software components accesses healthcare provider profiles 210a to determine how and where the electronic notification will be sent to the selected healthcare provider. For example, if an ultrasound manufacturer provided a recall of a particular ultrasound device to healthcare website 101, Physician Del Guidice would receive a facsimile notification while Physicians Fotsch and Choy would not receive a notification because they do not work with ultrasound equipment. Similarly, Physician Fotsch would receive an email notification of a recall of the drug lidocaine; while Physicians Del Guidice and Choy would not as their specialty and typically prescribed drugs indicate that they do not typically prescribe lidocaine.

In an embodiment, CME and MOC tests are provided to physicians by CM203 similar to healthcare notifications.

In an embodiment, database 210 includes records 210b having particular notifications associated with specialties, CME tests, correct CME answers and CME credits per test.

In an embodiment, database 210 includes records 210c having certification tests and answers associated with medication and/or medical devices that require certification.

In an embodiment, database 210 includes records 210d having MOC tests and answers associated with MOC specialties.

In an embodiment, database 210 includes a plurality of patient electronic health records associated with each physician. Each patient electronic health record includes information, such as prescribed drugs, medical conditions/allergies, age, certificates, etc., that allow healthcare website 101 to identify patients to receive particular healthcare notifications.

IV. HARDWARE ARCHITECTURE

Figure 4:
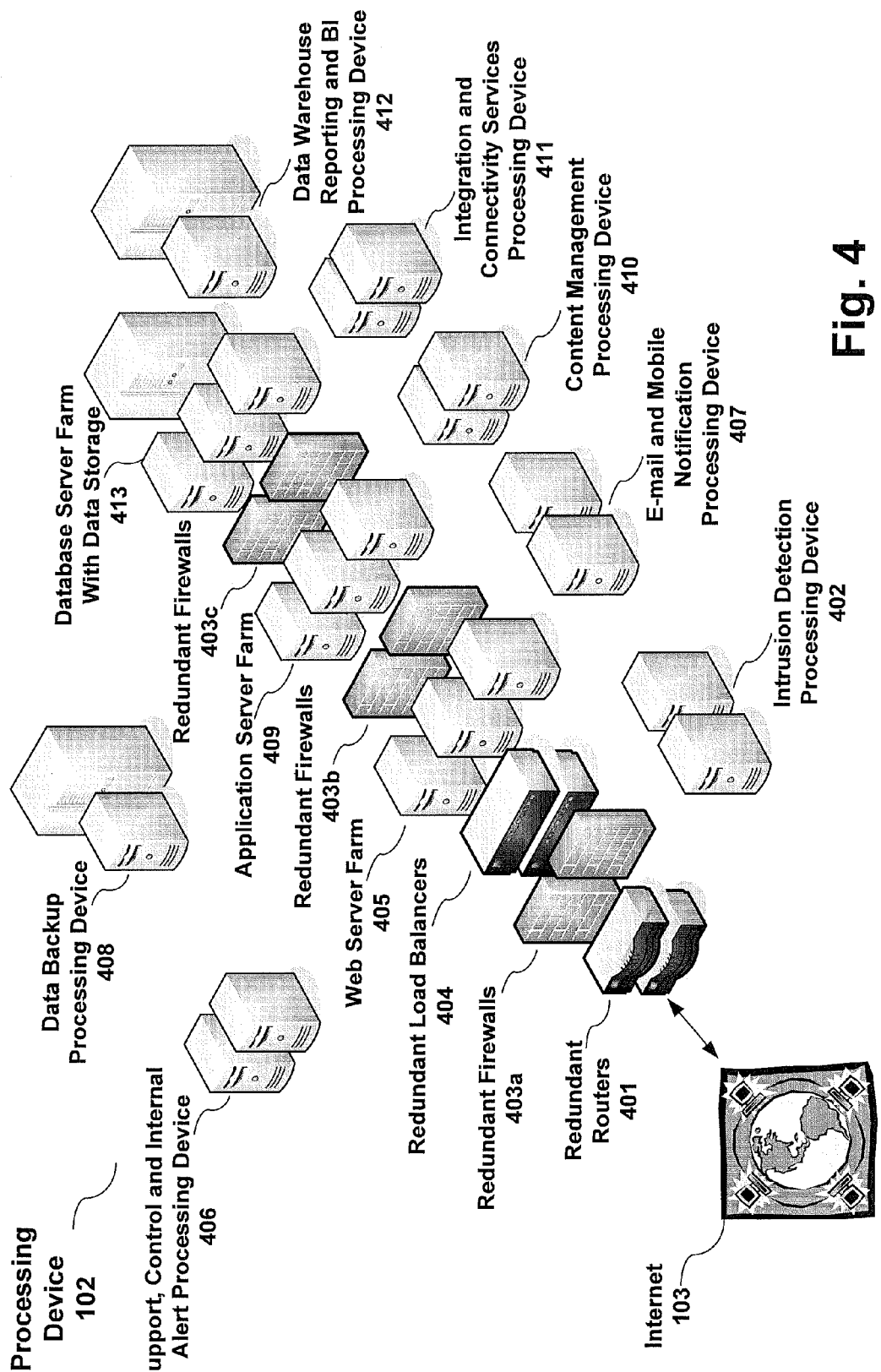
FIG. 4 illustrates a hardware architecture of healthcare platform processing device 102 shown in FIGS. 1A-B according to an embodiment.

FIG. 4 illustrates a hardware architecture embodiment of processing device 102 shown in FIG. 1.

Processing device 102 and software 102a operate under an Application Service Provider (ASP) model. Software is delivered from processing device 102 as services rather than a set of deliverables (s/w packages, executables, CDs, etc.) to processing devices 105a-b,104a-b, 152, 172 and 107 via Internet 103. Software offered using an ASP model may be called On-demand software or Software as a Service (SaaS). For example, access to an application program, such as Healthcare Portal software component 200 shown in FIG. 2A, using a standard protocol such as HTTP is provided by processing device 102. Applications are accessed by content consumers and content providers through a web browser on their respective processing devices using HTML or by special purpose client software which access interfaces exposed by processing device 102.

In embodiments, processing device 102 includes a large number of servers, networking equipment, other processing devices, sub-systems and/or equivalent hardware, designed to support uninterrupted functioning of software components and services. As one of ordinary skill in the art would appreciate, more or less processing devices shown in FIG. 4 may be used in alternate embodiments. In embodiments, one or more software components illustrated in FIG. 2A are at least partially stored and/or at least partially executed by processing devices illustrated in FIG. 4. In alternate embodiments, processing devices illustrated in FIG. 4 may be replaced by functionally equivalent software components.

Redundant routers 401 are coupled to Internet 103 and are responsible for routing messages, such as IP packets, between Internet 103 and the rest of processing device 102 or the local area network of processing devices illustrated as processing device 102 in an embodiment.

Redundant firewall 403a, coupled to redundant router 401, is responsible for, along with intrusion detection processing device 402, detecting unauthorized users (such as hackers and intruders) and preventing unauthorized users from accessing processing device 102.

Redundant firewalls 403b and 403c coupled to web server farm 405, application server farm 409 and database server farm with data storage 413 also are responsible for preventing unauthorized users from accessing processing device 102 and in particular application server farm 409 and database server farm with data storage 413.

Redundant load balancers 404, coupled to redundant firewall 403a, are responsible for providing a single Internet service from multiple servers and spread work among the multiple servers.

Support, Control and Internal Alert processing device 406 is responsible for controlling, reporting, auditing and notifications associated with processing device 102. In an embodiment, Support Control and Internal Alert processing device 406 is used to support and maintain availability of processing device 102. In an embodiment, support software component 208 is at least partially stored and/or executed by processing device 406.

Web server farm 405 includes a plurality of processing devices that accept HTTP requests from Internet 103 from healthcare providers and organizations as well as providing HTTP responses that may include data (such as HTML web pages/documents) to the healthcare providers and organizations. Web server farm 405 accesses other processing devices that may provide information and services. For example, Web server farm 405 may access email and mobile notification processing device 407 to generate an email healthcare notification to a particular set of healthcare providers stored in database server farm with data storage 413.

Email and mobile notification processing device 407 is responsible for generating email and mobile healthcare notifications to selected healthcare providers. Software components 201 and 202 are at least partially stored and/or executed by processing device 407.

Application server farm 409 includes a plurality of processing devices, coupled to redundant firewall 403b, that are responsible for delivering applications/services to processing devices coupled to Internet 103 using HTTP. Application server farm 409 is responsible for dynamic content and accessing database server farm with data storage 413. In an embodiment, healthcare portal 200 is at least partially stored and/or executed by application server farm 409.

Content Management processing device 410 is responsible for creating and maintaining of the content such as publishing, editorial workflow, as well as definition of target distribution criteria. In an embodiment, content management software component 204 is at least partially stored and/or executed by processing device 410.

Integration and connectivity services processing device 411 is responsible for integration with a variety of third party systems. Integration includes both publishing and subscription activities supporting two-way flow of the data. In an embodiment, IC software component 205 is at least partially stored and/or executed on processing device 411, Database server farm with data storage 413 includes a plurality of processing devices, coupled to redundant firewall 403c, that are responsible for accessing database software component 210 and rich media software component 209. In an embodiment, database server farm with data storage 413 accesses selected healthcare providers based on the content of healthcare related notifications provided by organizations and the healthcare provider profile. This selected list of healthcare providers along with associated electronic addresses are then passed to email and mobile notification processing device 407 to generate the appropriate notices to the appropriate electronic addresses.

Data warehouse reporting and BI processing device 412 is responsible for tracking and storing statistics, such as the number of acknowledgements and which healthcare providers had received healthcare related notifications and/or provided answers to survey questions. Organizations may access these statistics.

Data backup processing device 408 backs up or provides a duplicate of data and transactions performed in processing device 102.

Figure 7:
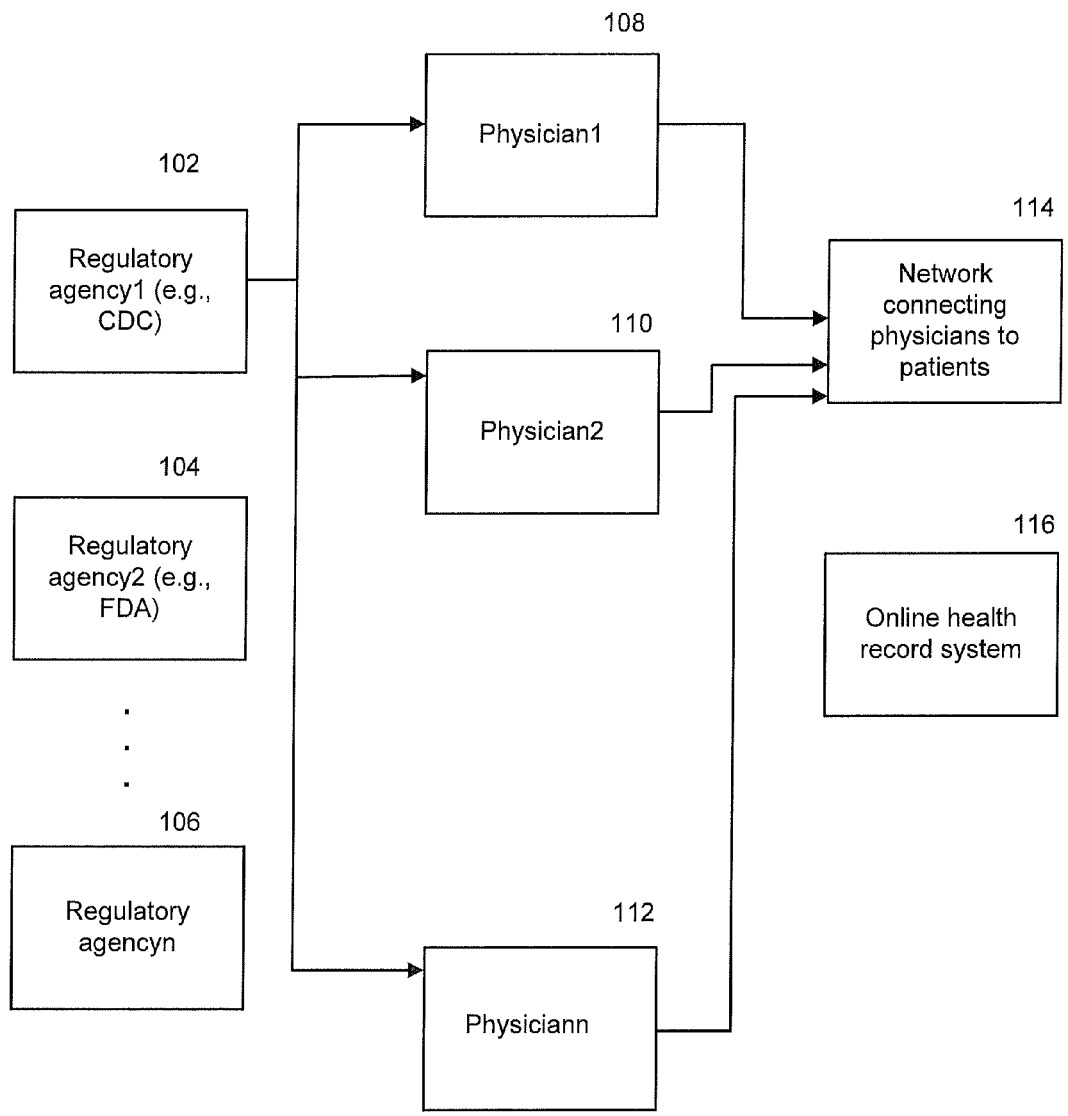
FIG. 7 is a diagram illustrating an exemplary system according to an embodiment.

FIG. 7 is a system diagram illustrating a system in which another embodiment may be implemented. Specifically, the system enables organizations to communicate with healthcare providers regarding health-related issues affecting patient health. The organizations may include any organizations with a need to communicate with healthcare providers (e.g., physicians) on a local, regional or national level regarding health-related issues affecting patient health, such as the CDC or FDA. The health-related issue may, for example, pertain to issues such as those related to a product (e.g. product recall), food, medical device, or a drug (e.g., drug recall or correction, such as a label change), an epidemic, or bioterrorism alert. Other examples may include newly discovered information about a medication such as drug interactions, use of the drug with patients with various medical disorders, or modifications to the proper dosage and administration of the drug.

In this example, a healthcare notification network enables communication on behalf of organizations such as regulatory agencies 102, 104, 106 to healthcare providers such as physicians 108, 110, 112. This may be accomplished, for example, through registration of the organizations and physicians with the network. In this manner, regulatory agencies such as the FDA or the CDC may communicate with healthcare providers such as physicians.

While it is possible that email may be used to support communication between the regulatory agencies 102, 104, 106 and the healthcare providers 108, 110, 112, there is currently no national professional healthcare email network. Through the use of a healthcare notification network, healthcare providers may access communications from these agencies. Similarly, the agencies may also receive responses from the healthcare providers, via the network, in response to the notifications. These communications may be secured (e.g., via username and password) or unsecured. The healthcare notification network enables notifications to be composed and delivered to physicians via email, as well as acknowledgements to be delivered back to the network, and then on to the organizations in response to the notifications, as will be described in further detail below.

In the example shown in FIG. 7, the regulatory agency 102 (e.g., CDC) sends an electronic notification for a particular health-related issue to the network, for distribution to one or more healthcare providers. The electronic notification may also include a mechanism for obtaining an acknowledgement indicating, at minimum, that the healthcare provider has received and opened the electronic notification. In this manner, the regulatory agency 102 may receive information from the network regarding an acknowledgement from the healthcare provider indicating that the healthcare provider has received and opened the electronic notification. The acknowledgement may also indicate that the healthcare provider has read the electronic notification, as well as indicate that the healthcare provider has followed or agrees to follow the instructions in the notification and/or that the healthcare provider has notified or will notify patients affected by the health-related issue. Other organizations 104, 106 (e.g., companies or regulatory agencies) may transmit or have electronic notifications transmitted and receive acknowledgements in a similar manner. From the acknowledgements (or reports thereon), the organizations 102, 104, 106 may compile the appropriate reports in compliance with FDA and CDC regulations.

Once a healthcare provider (e.g., physician) has been notified of a particular health-related issue, they should notify the appropriate patients. This may be accomplished, for example, by notifying the patients via a network 114 connecting the physician(s) to their patients. In other words, the network 114 may be a network to which the healthcare provider and their patients belong. This notification may be a new notification message that is automatically generated or manually composed by the healthcare provider. Alternatively, the healthcare provider may choose to forward the notification received by the healthcare provider to the affected patients, when an organization has given the physician a notification that is appropriate for distribution to patients. The network 114 may be a part of the network that enables communication between the organizations and the healthcare providers or, alternatively, the network 114 may be a separate network connecting the healthcare providers to their patients. One such network connecting healthcare providers with patients is described in further detail in Attorney Docket No. MEDE-01000US0, patent application Ser. No. 10/387,041, entitled "HEALTHCARE PROVIDER-PATIENT ONLINE CONSULTATION SYSTEM," filed on Mar. 10, 2003, naming Fotsch et al as inventors, which is incorporated herein by reference for all purposes. Through this network, secure and confidential communications between healthcare providers and patients is supported (e.g., via registration and login using a username/user ID and password).

The healthcare provider may send an appropriate notification message to all of his or her patients. Alternatively, the healthcare provider may identify the patients affected by the particular health-related issue identified in the notification message received by the healthcare provider. In order to identify the affected patients, the healthcare provider may search an online health record system 116 storing health records for a plurality of patients to identify the subset of his or her patients affected by the particular health-related issue. For instance, the healthcare provider may search the online health record system 116 for patients affected by a particular medical condition and/or taking a particular medication. An exemplary online health record system is described in further detail in Attorney Docket No. MEDE-01000US2, patent application Ser. No. 11/085,984, entitled "ELECTRONIC PERSONAL HEALTH RECORD SYSTEM," filed on Mar. 21, 2005, naming Fotsch et al as inventors. In this manner, a healthcare provider may identify a segment of their patients affected by the health-related issue identified in a notification received from an organization such as the FDA or the CDC.

The electronic notification may be implemented in a variety of forms, and in accordance with a variety of formats and protocols. For instance, the electronic notification may be sent in the form of an electronic mail message. The electronic notification (e.g., electronic mail message) may also include a link to a web page that includes at least a part of the content of the electronic notification. The electronic mail message containing the notification can be sent to a computer email system, a pager, a cell phone, or other device, or some combination of the above, that will enable immediate access to the information by the healthcare provider.

Similarly, the acknowledgement may be transmitted by a healthcare provider to the network or organization that transmitted the electronic notification in a variety of forms, and in accordance with a variety of formats and protocols. For instance, the acknowledgement may be sent in the form of an electronic mail, or may be submitted via a website such as that referenced in the link from the electronic notification.

It is also important to note that the acknowledgement may also be sent automatically to the network or organization in the form of an automated response, as well as in response to input by the healthcare provider. For instance, an automated response may be implemented via a HTML tag, as will be described in further detail below. This is particularly useful, for example, in notifying the network, and then the organization, that the healthcare provider has received and opened the corresponding notification, since the healthcare provider may not be required to respond to a particular notification, or forget to respond to the notification. FIGS. 8A-D present exemplary mechanisms for transmitting a notification to a healthcare provider, as well as exemplary mechanisms for obtaining an acknowledgement from the healthcare provider.

It is important to note that, while conventional email systems may be used to transmit notifications, FDA regulations currently require that notifications sent to physicians use specific font sizes and colors. In order to fulfill such requirements, in accordance with one embodiment, HTML-type viewing of the notification is supported. This may be accomplished via a HTML email or an email with a link to a HTML web page.

Figure 8A:
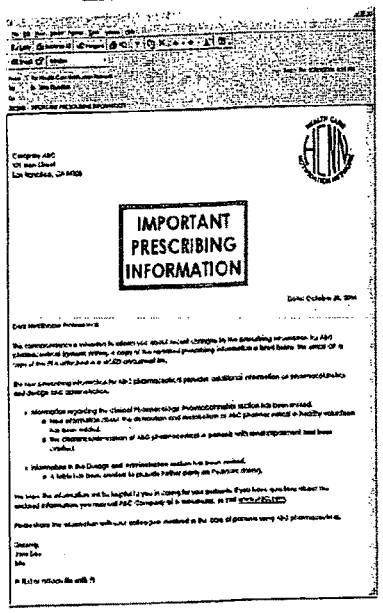
FIG. 8A illustrates an exemplary HTML email including a notification that may be transmitted to healthcare providers.

In accordance with various embodiments, a notification email may be sent in HTML format, as well as non-HTML format. FIG. 8A is an exemplary HTML email including a notification that may be transmitted to healthcare providers. This exemplary email pertains to prescribing information. Specifically, in this example, new information about the distribution and metabolism of the identified drug is provided. In addition, the effect of the medication on patients with renal impairment is clarified, and information regarding the dosage and administration of the drug is clarified with respect to pediatric dosing.

In accordance with one embodiment, if the recipient has a HTML-capable email application, the HTML email will be opened and a HTML tag in the HTML email will report receipt back to the healthcare notification network, thereby supporting automated acknowledgement in response to the notification. In some embodiments or if the recipient's email application is not HTML-capable, the recipient receives a simple message (in HTML or non-HTML format) that an important patient safety message is available through a hypertext link embedded in the email. The recipient then clicks on the link and is taken to a HTML web page. At that time, a HTML tag may be reported to the healthcare notification network. In accordance with one embodiment, the HTML tag will carry the information necessary to accurately identify the healthcare provider.

Figure 8B:
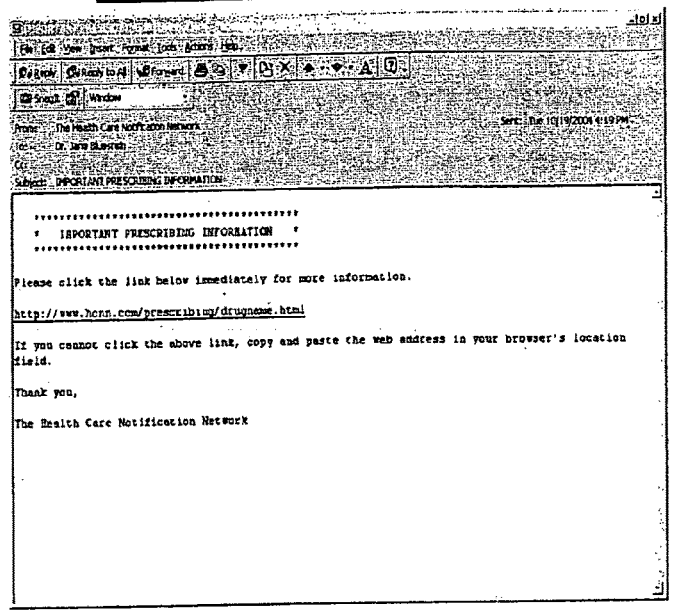
FIG. 8B illustrates an exemplary non-HTML email with a link to an HTML web page including notification that may be transmitted to healthcare providers.

As set forth above, rather than providing the relevant information in the email itself, the information (or portion thereof) may be provided in a separate web page. FIG. 8B is an exemplary non-HTML email with a link to a HTML web page including a notification that may be transmitted to healthcare providers. In this example, the notification is not provided in the email, but in the web page. Thus, the user must access the web page referenced in the email to read the notification.

Figure 8C:
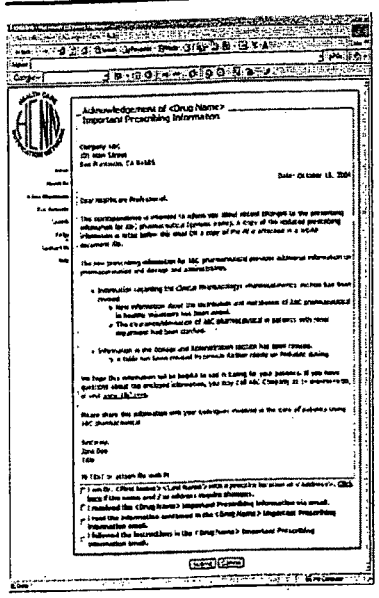
FIG. 8C illustrates an exemplary HTML web page with notification and physician response survey that may be transmitted to healthcare providers.

As set forth above, a HTML notification may be provided in the form of a link to a HTML web page or HTML email. FIG. 8C is an exemplary HTML web page with notification and physician response survey that may be transmitted to healthcare providers, while FIG. 8D is an exemplary HTML notification with a physician response survey that may be transmitted to healthcare providers.

Figure 8D:
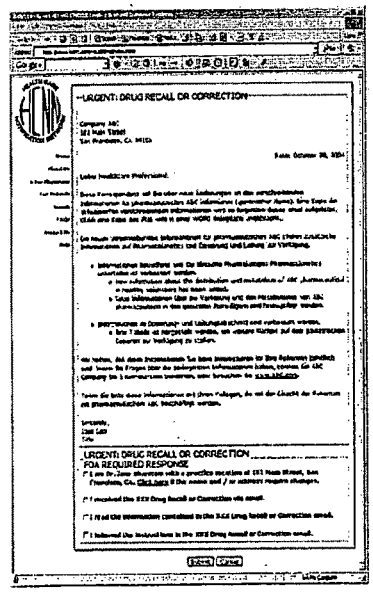
FIG. 8D illustrates an exemplary HTML notification with a physician response survey that may be transmitted to healthcare providers.

As shown in both FIGS. 8C and 8D, the notification may include a mechanism for obtaining an acknowledgement, which may be in the form of a physician response survey (as shown). The physician response survey may be accessed when the user accesses the web page (as shown), or alternatively, may be accessed when the user reads the electronic notification (e.g., email). The physician response survey includes one or more questions or entries requiring a response by the healthcare provider.

In this example, the physician response survey enables a healthcare provider to confirm his or her identity, as well as submit any name or address changes. Moreover, the healthcare provider may indicate that he or she has followed or will follow the instructions provided in the electronic notification (as shown), or more specifically, the healthcare provider may indicate that he or she has notified or will notify patients affected by the health-related issue.

The above-described embodiments may be used to notify healthcare providers (e.g., physicians) of issues affecting patient health. Thus, the notifications and content thereof may comply with FDA and/or CDC regulations. For instance, FDA regulations may be found in the ORA/Office of Enforcement, Division of Compliance Management and Operations Guidance for Industry, Product Recalls, including Removals and Corrections, which may be found at HTTP://www.fda.gov/ora/compliance_ref/recalls/ggp_recall.htm, which is incorporated herein by reference. In accordance with such regulations, information may include a description or identification of the product that is the subject of the notification. The description or identifying information may include information such as the identity of the manufacturer, as well as the identity of the recalling firm (e.g., manufacturer, importer, broker, repacker, or own-label distributor). The information provided in the notification may also include the identity of the firm responsible for the violation or problem, as well as the reason for the recall or notification. Furthermore, the notification may also include a health hazard assessment including an assessment of the health risk. Finally, the notification may provide instructions to the patients, such as returning the product, discontinued use of the product, or modification of dosage or other instructions for modified use of the product in accordance with the notification.

FIG. 9 is a block diagram of a hardware environment in which the various embodiments of the healthcare notification network may be implemented in order to facilitate communication between organizations and healthcare providers. The healthcare notification network through which communications between organizations and one or more physicians are facilitated according to an embodiment and the network itself through which these notifications are sent may be include a server 2002, which is connected by a router 2004 to the Internet 2006. Employees of the network at computers 2003 may be coupled to the server 2002 to receive communications from organizations. Once the employees review the communications and deemed them appropriate for transmission, they may transmit them to healthcare providers by the router 2004 via the Internet 2006.

In addition, physician office computers 2008 may also be connected to the Internet via routers 2010 in order to receive the transmission of emails from the server 2002 and transmit acknowledgement messages to the server 2002 (e.g., via answering a survey or automatically). The physician office computers 2008 may run software as well as store messages such as notification messages received by the physicians. Physician office computers 2008 may have networks 2012 associated therewith interconnecting a plurality of personal computers or work stations 2014. In this manner, an office network may access received emails from the email client through the server 2002. Organizations (e.g., agencies) (represented by computers 2022 and 2024) may be connected to the Internet in a variety of ways for transmission of messages to the network. For example, an agency worker employed by an agency may be connected from his home via a modem 2026, or from his workplace via a network 2020, a file server 2016, and a router 2018. It will be understood that, according to various embodiments of the invention, employees of such organizations or agencies may gain access to the Internet for transmission of information to the network and then on to the healthcare provider via a variety of hardware configurations. Similarly, such employees may be coupled to a website on server 2002 in order to gain access to the server 2002 and to initiate the transmission of communications such as email notifications to the network, for distribution to one or more physicians. Similarly, an employee may access the network 2002 or website from his computer 2014 at his place of employment. It will also be understood that the hardware environment of FIG. 9 is shown for illustrative purposes and that a wide variety of hardware environments may be employed to implement the various embodiments of the present invention. It should also be understood that specific embodiments of the methods and processes described herein may be implemented as computer program instructions, i.e., software, in the memory of the computers and servers.

Although illustrative embodiments are shown and described herein, many variations and modifications are possible which remain within the concept, scope, and spirit of the claims, and these variations would become clear to those of ordinary skill in the art after perusal of this application. For instance, an embodiment is based upon the generation and transmission of notification messages via email and/or website. However, it should be understood that embodiments are not limited to this arrangement, but instead would equally apply regardless of the mode of transmission or system configuration, including the use of pagers, cell phones, or other instruments as receiving devices for the notifications. Accordingly, the present embodiments are to be considered as illustrative and not restrictive, and the invention is not to be limited to the details given herein, but may be modified within the scope and equivalents of the appended claims.

What is claimed is:

1. A method performed by a processing device to notify a plurality of physicians of a medical event, the method comprising:

receiving, by the processing device, electronic information indicating the medical event, wherein the medical event is selected from a group consisting of a drug recall, a medical device recall, a drug usage warning, a medical device warning, a medical equipment recall, a medical equipment warning, a biological threat and a communicable threat;

selecting, by the processing device, a set of the plurality of physicians to notify in response to a type of medical event, wherein the selecting includes selecting the set from a database of physician names;

selecting, by the processing device, a test to be completed by a physician in the set of physicians in order to earn credit toward continuing medical education requirements; preparing, by the processing device, an electronic healthcare notification of the medical event to the set of physicians;

providing, by the processing device, the electronic healthcare notification to the set of physicians;

providing, by the processing device, the test to each of the physicians in the set of physicians, wherein the test is related to information in the electronic healthcare notification, wherein the test includes a plurality of multiple choice questions, and wherein a plurality of answers to the plurality of multiple choice questions by the at least one physician indicates that the physician understood the content of the information in the electronic healthcare notification;

receiving, by the processing device, the plurality of answers to the test provided by at least one of the physicians in the set of physicians;

comparing, by the processing device, the plurality of answers with a plurality of correct answers; and assigning, by the processing device, a credit value to the at least one physician in response to the comparing.

2. The method of claim 1, wherein the selecting the set of physicians is based on a medical specialty and the selecting the test is based on a content of the electronic healthcare notification.

3. The method of claim 1, wherein the providing the electronic healthcare notification includes generating an email message to the at least one physician in the set of physicians, wherein the email message includes a hyperlink to a website that includes a content of the healthcare notification.

4. The method of claim 2, wherein the providing the test includes providing a web page at a website, the web page including the plurality of multiple choice questions regarding the content of the electronic healthcare notification.

5. The method of claim 1, further comprising:

selecting, by the processing device, a type of electronic notification to provide to each of the physicians in the set of physicians; and formatting, by the processing device, the information indicating the medical event in response to a selected type of electronic notification, wherein providing the electronic healthcare notification includes notifying each of the physicians in the set of physicians by the respective selected type of electronic notification.

6. The method of claim 1, wherein receiving the electronic information includes receiving information from an entity selected from a group consisting of a pharmaceutical company, a medical device manufacturer, a medical equipment manufacturer and a government agency.

7. A method of operation in a system including at least one processing device to execute machine readable instructions and at least one storage device to store a plurality of physician names, a plurality of respective specialties and a plurality of tests, the method comprising:

receiving electronic information indicating a medical event;

selecting, by the at least one processing device in response to 1) the machine readable instructions, 2) a type of the medical event and 3) the plurality of specialties, a set of the plurality of physician names to notify from the at least one storage device;

wherein the medical event is selected from a group consisting of a drug recall, a medical device recall, a drug usage warning, a medical device warning, a medical equipment recall, a medical equipment warning, a biological threat and a communicable threat, wherein the plurality of physician names is stored in a database; selecting, by the processing device in response to the machine readable instructions, a test from the plurality of tests, stored in the storage device, to be completed by a at least one physician from the set of physician names in order to earn credit toward continuing medical education requirements;

preparing, by the processing device in response to the machine readable instructions, an electronic healthcare notification of the medical event to a set of physicians corresponding to the set of physician names;

providing the electronic healthcare notification to the set of physicians;

providing the test to each of the physicians in the set of physicians, wherein the test includes a plurality of multiple choice questions, and wherein a plurality of answers to the plurality of multiple choice questions by at least one physician in the set of physicians indicates that the physician understood the content of the information in the electronic healthcare notification; and receiving answers to the test provided by at least one of the physicians in the set of physicians:

comparing, by the at least one processing device in response to the machine readable instructions, the received answers with the plurality of correct answers; and assigning, by the at least one processing device in response to the machine readable instructions, a credit value to the at least one physician in the set of physicians in response to the comparing.

8. The method of claim 7, wherein the providing the electronic healthcare notification includes generating an email message to the at least one physician in the set of physicians, wherein the email message includes a hyperlink to a website that includes a content of the electronic healthcare notification.

9. The method of claim 7, wherein the providing the test includes providing a web page at a website, the web page including a plurality of multiple choice questions regarding a content of the electronic healthcare notification.

10. A system to provide information regarding a medical event, the system comprising: at least one storage device to store a plurality of physician names in a database, a plurality of respective specialties and a plurality of tests to earn continuing education credit; at least one processor, coupled to the storage device;

the at least one storage device to store executable machine readable instructions for controlling the processor; and the at least one processor is operative with the executable machine readable instructions to:

receive information regarding the medical event, wherein the medical event is selected from a group consisting of a drug recall, a medical device recall, a drug usage warning, a medical device warning, a medical equipment recall, a medical equipment warning, a biological threat and a communicable threat;

select a set of physicians to receive information regarding the medical event from the plurality of physician names;

select a preferred type of communication for each of the physicians in the set of physicians;

format the information regarding the medical event in response to the preferred type of communication for each of the physicians in the set of physicians;

provide an electronic notification of the information regarding the medical event to each of the physicians in the set of physicians, each electronic notification formatted based on the corresponding preferred type of communication;

select a test from the plurality of tests to provide to each of the physicians in the set of physicians;

provide the test to each of the physicians in the set of physicians, wherein the test includes a plurality of multiple choice questions, and wherein a plurality of answers to the plurality of multiple choice questions by each of the physicians in the set of physicians indicates that each respective physician understood the content of the information in the electronic notification;

receive answers to the test provided by at least one of the physicians in the set of physicians;

compare the received answers with a plurality of correct answers; and assign a credit value to the at least one of the physicians in the set of physicians in response to the comparison of the provided answers with the plurality of correct answers.

11. The system of claim 10, wherein the provided electronic notification includes generating an email message to the at least one physician in the set of physicians, wherein the email message includes a hyperlink to a website that includes information regarding the medical event.

12. The system of claim 11, wherein the provided test includes a web page at a website, the web page having a plurality of multiple choice questions regarding the medical event.

13. A method performed by a processing device to notify a plurality of physicians of a medical event, the method comprising:

receiving, by the processing device, electronic information regarding the medical event, wherein the medical event is selected from a group consisting of a drug recall, a medical device recall, a drug usage warning, a medical device warning, a medical equipment recall, a medical equipment warning, a biological threat and a communicable threat;

selecting, by the processing device, a set of the plurality of physicians to notify in response to a type of medical event and in response to whether a physician has received an electronic healthcare notification of the medical event, wherein the plurality of physicians is obtained from a database of physician names;

preparing, by the processing device, an electronic healthcare notification of the medical event for the set of physicians;

providing, by the processing device, the electronic healthcare notification to the set of physicians;

providing a test to each of the physicians in the set of physicians, wherein the test includes a plurality of multiple choice questions, and wherein a plurality of answers to the plurality of multiple choice questions by each of the physicians in the set of physicians indicates that each respective physician understood the content of the information in the electronic healthcare notification;

comparing, by the at least one processing device in response to the machine readable instructions, the received answers with the plurality of correct answers; and assigning, by the at least one processing device in response to the machine readable instructions, a credit value to the at least one physician in the set of physicians in response to the comparing.

14. The method of claim 13, wherein the providing includes providing the electronic healthcare notification to a website that provides electronic prescriptions for the set of physicians.

15. The method of claim 13, wherein the providing includes providing the electronic healthcare notification to a website that provides electronic healthcare records for the set of physicians.

16. The method of claim 13, wherein the providing includes providing a notification to register at a website in order to obtain the electronic healthcare notification.

17. The method of claim 13, wherein the providing includes providing a hyperlink to a website in order to obtain the electronic healthcare notification.

18. The method of claim 13, wherein the selecting the set of physicians is based on a medical specialty of the physician and the selecting is based on whether the physician in the plurality of physicians has received an email regarding the electronic healthcare notification.

19. A system to provide information regarding a medical event, the system comprising:

at least one storage device to store a plurality of physician names, a plurality of respective specialties and respective associated healthcare websites, wherein the plurality of physician names is stored in a database;

at least one processor, coupled to the storage device;

the at least one storage device to store executable machine readable instructions for controlling the processor; and the at least one processor is operative with the executable machine readable instructions to:

receive electronic information regarding the medical event, wherein the medical event is selected from a group consisting of a drug recall, a medical device recall, a drug usage warning, a medical device warning, a medical equipment recall, a medical equipment warning, a biological threat and a communicable threat;

select a set of physicians from the plurality of physician names to notify in response to a type of medical event and in response to respective specialties of the plurality of physicians; provide an electronic notification of the information regarding the medical event to each of the physicians in the set of physicians at the respective associated healthcare websites;

provide a test to each of the physicians in the set of physicians, wherein the test includes a plurality of multiple choice questions, and wherein a plurality of answers to the plurality of multiple choice questions by each of the physicians in the set of physicians indicates that each respective physician understood the content of the information in the electronic notification;

compare the received answers with a plurality of correct answers; and assign a credit value to the at least one of the physicians in the set of physicians in response to the comparison of the provided answers with the plurality of correct answers.

20. The system of claim 19, wherein the at least one storage device, at least one processor and executable machine readable instructions provide a healthcare website that provides electronic information regarding the medical event, and wherein the electronic notification includes a hyperlink to the healthcare website.

21. The system of claim 20, wherein the respective associated healthcare websites include at least one of an electronic prescription website and an electronic medical records website.

22. The system of claim 19, wherein the at least one storage device, at least one processor and executable machine readable instructions provide a healthcare website that provides electronic information regarding the medical event, and wherein the electronic notification includes a notification to register at the healthcare website in order to obtain the electronic healthcare notification.

23. A system to provide notification of a medical event to a physician, the system comprising:
   a first processing device including a processor to execute machine readable instructions stored on a storage device, the first processing device to access notification of the medical event from a healthcare website;
   a second processing device including a processor to execute machine readable instructions stored on a storage device, the second processing device to provide the healthcare website that provides the notification of the medical event, the second processing device to provide a test to the physician, wherein the test includes a plurality of multiple choice questions, and wherein a plurality of answers to the plurality of multiple choice questions by the physician indicates that the physician understood the content of the notification of the medical event the second processing device further comparing in response to the machine readable instructions, the received answers with the plurality of correct answers, and assigning, by the at least one processing device in response to the machine readable instructions, a credit value to the at least one physician in the set of physicians in response to the comparing; and
   a third processing device including a processor to execute machine readable instructions stored on a storage device, the third processing device to provide an associated healthcare website that receives an indication that the notification of the medical event is available at the healthcare website,
   wherein the medical event is selected from a group consisting of a drug recall, a medical device recall, a drug usage warning, a medical device warning, a medical equipment recall, a medical equipment warning, a biological threat and a communicable threat, and
   wherein the physician is obtained from a database storing a plurality of physician names.

24. The system of claim 23, wherein the first processing device is used by the physician to access the notification of the medical event.

25. The system of claim 23, wherein the associated healthcare website includes at least one of an electronic prescription website and an electronic medical records website.

26. The system of claim 25, wherein the indication that the notification of the medical event is available includes a hyperlink to the notification of the medical event.

27. The system of claim 23, wherein the indication that the notification of the medical event is available includes notification to register at the healthcare website in order to obtain the notification of the medical event.

28. The system of claim 23, wherein the second processing device provides the indication that the notification of the medical event is available at the healthcare website to the third processing device when the second processing device has not sent an email regarding the medical event to the first processing device.

29. The method of claim 1, wherein in the database of physician names is an industry recognized validated database of physicians.

30. The method of claim 1, wherein the database of physician names has been registered by a medical society.

* * * * *